United States Patent
Demore et al.

(10) Patent No.: US 12,258,388 B2
(45) Date of Patent: Mar. 25, 2025

(54) COMPOSITIONS AND METHODS COMPRISING SFRP2 ANTAGONISTS

(71) Applicant: The University of North Carolina at Chapel Hill, Chapel Hill, NC (US)

(72) Inventors: Nancy Demore, Mount Pleasant, SC (US); Cam Patterson, Little Rock, AR (US)

(73) Assignee: The University of North Carolina at Chapel Hill, Chapel Hill, NC (US)

(*) Notice: Subject to any disclaimer, the term of this patent is extended or adjusted under 35 U.S.C. 154(b) by 0 days.

(21) Appl. No.: 18/412,245

(22) Filed: Jan. 12, 2024

(65) Prior Publication Data

US 2024/0190949 A1    Jun. 13, 2024

Related U.S. Application Data

(62) Division of application No. 17/547,550, filed on Dec. 10, 2021, now Pat. No. 11,873,333.

(60) Provisional application No. 63/124,345, filed on Dec. 11, 2020.

(51) Int. Cl.
| | | |
|---|---|---|
| *C07K 16/18* | (2006.01) | |
| *A61K 39/00* | (2006.01) | |
| *A61P 35/00* | (2006.01) | |
| *C07K 16/28* | (2006.01) | |
| *C07K 16/30* | (2006.01) | |

(52) U.S. Cl.
CPC .............. *C07K 16/18* (2013.01); *A61P 35/00* (2018.01); *C07K 16/2818* (2013.01); *C07K 16/3015* (2013.01); *C07K 16/303* (2013.01); *A61K 2039/505* (2013.01); *C07K 2317/24* (2013.01)

(58) Field of Classification Search
CPC ............... C07K 16/18; C07K 16/2818; C07K 16/3015; C07K 16/303; C07K 2317/24; A61P 35/00; A61K 2039/505
See application file for complete search history.

(56) References Cited

U.S. PATENT DOCUMENTS

| | | |
|---|---|---|
| 5,122,464 A | 6/1992 | Wilson et al. |
| 5,225,539 A | 7/1993 | Winter |
| 5,693,780 A | 12/1997 | Newman et al. |
| 5,807,715 A | 9/1998 | Morrison et al. |
| 5,965,726 A | 10/1999 | Pavlakis et al. |
| 6,174,666 B1 | 1/2001 | Pavlakis et al. |
| 6,291,664 B1 | 9/2001 | Pavlakis et al. |
| 6,414,132 B1 | 7/2002 | Pavlakis et al. |
| 6,794,498 B2 | 9/2004 | Pavlakis et al. |
| 8,734,789 B2 | 5/2014 | Demore et al. |
| 9,073,982 B2 | 7/2015 | Demore et al. |
| 11,873,333 B2 | 1/2024 | Demore et al. |
| 2004/0014194 A1 | 1/2004 | Beyer et al. |
| 2022/0204598 A1 | 6/2022 | Demore et al. |

FOREIGN PATENT DOCUMENTS

| | | |
|---|---|---|
| WO | WO-8605807 A1 | 10/1986 |
| WO | WO-8901036 | 2/1989 |
| WO | WO-2009036379 A2 | 3/2009 |
| WO | WO-2010105256 A1 | 9/2010 |
| WO | WO-2011119524 A1 | 9/2011 |
| WO | WO-2012009568 A2 | 1/2012 |
| WO | WO-2012145493 A1 | 10/2012 |
| WO | WO-2015038882 A1 | 3/2015 |
| WO | WO-2022125927 A1 | 6/2022 |

OTHER PUBLICATIONS

Garcia, D., et al., "Development of a Novel Humanized Monoclonal Antibody to Secreted Frizzled-related Protein-2 That Inhibits Triple-negative Breast Cancer and Angiosarcoma Growth in Vivo," Annals of Surgical Oncology 26(13):4782-4790, Springer, United States (Dec. 2019).
International Search Report for International Application No. PCT/US2021/062854, International Search Authority, United States, mailed on May 16, 2022, 5 pages.
Bhati, R., et al., "Molecular Characterization of Human Breast Tumor Vascular Cells," The American Journal of Pathology 172(5):1381-1390, Elsevier, United States (May 2008).
Champe, M., et al., "Monoclonal Antibodies that Block the Activity of Leukocyte Function-Associated Antigen I Recognize Three Discrete Epitopes in the Inserted Domain of CDlla," The Journal of Biological Chemistry 270 (3):1388-1394, Elsevier Inc. on behalf of American Society for Biochemistry and Molecular Biology, United States (Jan. 1995).
Chayen, N.E., "The Role of Oil in Macromolecular Crystallization," Structure 5(10):1269-1274, Cell Press, United States (Oct. 1997).
Chothia, C., et al., "Conformations of Immunoglobulin Hypervariable Regions," Nature 342(6252):877-883, Nature Publishing Group, United Kingdom (Dec. 1989).
Fontenot, E., et al., "A Novel Monoclonal Antibody to Secreted Frizzled-related Protein 2 Inhibits Tumor Growth," Molecular Cancer Therapeutics 12(5):685-695, American Association for Cancer Research Inc, United States (May 2013).

(Continued)

*Primary Examiner* — Mark Halvorson
*Assistant Examiner* — Dennis J Sullivan
(74) *Attorney, Agent, or Firm* — Jenkins, Taylor & Hunt, P.A.

(57) ABSTRACT

The present disclosure provides humanized antibodies and antigen-binding fragments thereof that specifically bind to SFRP2 and compositions comprising such humanized antibodies or antigen-binding fragments thereof. In some aspects, the humanized antibodies or antigen-binding fragments can be used to treat diseases or conditions associated with increased SFRP2, such as cancer. In some aspects, the antibodies or antigen-binding fragments can be used to treat osteosarcoma.

Figure 1A:
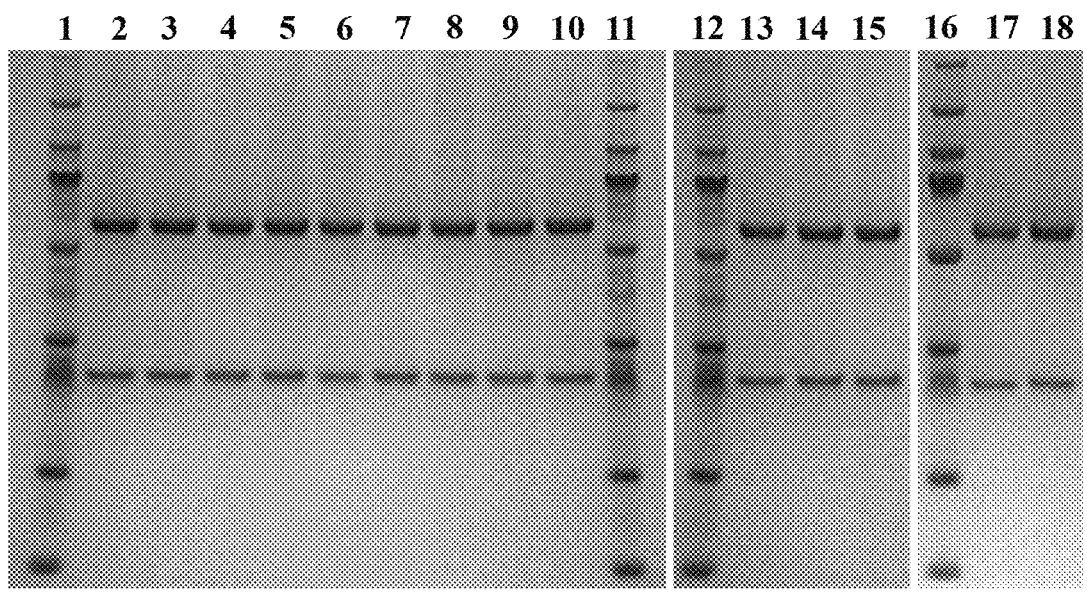

5 Claims, 15 Drawing Sheets
Specification includes a Sequence Listing.

(56) References Cited

OTHER PUBLICATIONS

International Search Report and Written Opinion for International Application No. PCT/US2021/062854, International Search Authority, United States, mailed on May 16, 2022, 11 pages.
Jones, P.T., et al., "Replacing the Complementarity-determining Regions in a Human Antibody with those from a Mouse," Nature 321(6069):522-525, Nature Publishing Group, United Kingdom (May 1986).
Kaur, A., et al., "sFRP2 in the Aged Microenvironment Drives Melanoma Metastasis and Therapy Resistance," Nature 532(7598):250-254, Nature Publishing Group, United Kingdom (Apr. 2016).
Kim, H., et al., "Oncogenic Role of SFRP2 in P53-Mutant Osteosarcoma Development via Autocrine and Paracrine Mechanism," Proceedings of the National Academy of Sciences of the United States of America 115(47):E11128-E11137, National Academy of Sciences, United States (Nov. 2018).
Kohler, G., and Milstein, C., "Continuous Cultures of Fused Cells Secreting Antibody of Predefined Specificity," Nature 256(5517):495-497, Nature Publishing Group, United Kingdom (Aug. 1975).
Koirala, P., et al., "Immune Infiltration and PD-L1 Expression in the Tumor Microenvironment Are Prognostic in Osteosarcoma," Scientific Reports 6:30093, pp. 1-10, Nature Publishing Group, United Kingdom (Jul. 2016).
Lee, J.L., et al., "Secreted Frizzled-related Protein 2 (Sfrp2) Is Highly Expressed in Canine Mammary Gland Tumors but Not in Normal Mammary Glands," Breast Cancer Research and Treatment 84(2):139-149, Kluwer Academic, Netherlands (Mar. 2004).
Lee, J.L., et al., "Secreted Frizzled Related Protein 2 (sFRP2) Decreases Susceptibility to UV-induced Apoptosis in Primary Culture of Canine Mammary Gland Tumors by NF-kappaB Activation or JNK Suppression," Breast Cancer Research and Treatment 100(1):49-58, Kluwer Academic, Netherlands (Nov. 2006).
Lindsey, B.A., et al., "Osteosarcoma Overview," Rheumatology and Therapy 4(1):25-43, Springer Healthcare, United Kingdom (Jun. 2017).
McPherson, A., "Crystallization of Proteins From Polyethylene Glycol," The Journal of Biological Chemistry 251(20):6300-6303, Elsevier Inc. on behalf of American Society for Biochemistry and Molecular Biology, United States (Oct. 1976).
McPherson, A., "Current Approaches to Macromolecular Crystallization," European Journal of Biochemistry 189(1):1-23, Blackwell Science Ltd, United Kingdom (Apr. 1990).
Oshima, T., et al., "Myeloma Cells Suppress Bone Formation by Secreting a Soluble Wnt Inhibitor, sFRP-2," Blood 106(9):3160-3165, Elsevier, United States (Nov. 2005).
Roguska, M.A., et al., "Humanization of Murine Monoclonal Antibodies through Variable Domain Resurfacing," Proceedings of the National Academy of Sciences USA 91(3):969-973, National Academy of Sciences, United States (Feb. 1994).
Roguska, M.A., et al., "A Comparison of Two Murine Monoclonal Antibodies Humanized by CDR-grafting and Variable Domain Resurfacing," Protein Engineering 9(10):895-904, Oxford University Press, United Kingdom (Oct. 1996).
Roversi, P., et al., "Modelling Prior Distributions of Atoms for Macromolecular Refinement and Completion." Acta Crystallographica. Section D, Biological Crystallography 56(Pt10):1316-1323, Wiley-Blackwell, United States (Oct. 2000).
Sambrook, J., and Russell, D.W., *Molecular Cloning: A Laboratory Manual*, 3rd Edition, Cold Spring Harbor Laboratory Press, Cold Spring Harbor, United States (2001).
Sun, Y., et al., "SFRP2 Augments WNT16B Signaling to Promote Therapeutic Resistance in the Damaged Tumor Microenvironment," Oncogene 35(33):4321-4334, Nature Publishing Group, United Kingdom (Aug. 2016).
Tanaka, M., et al., "Modeling Alveolar Soft Part Sarcoma Unveils Novel Mechanisms of Metastasis," Cancer Research 77(4):897-907, American Association for Cancer Research, United States (Feb. 2017).
Tawbi, H.A., et al., "Pembrolizumab in Advanced Soft-Tissue Sarcoma and Bone Sarcoma (SARC028): A Multicentre, Two-Cohort, Single-Arm, Open-Label, Phase 2 Trial," The Lancet. Oncology 18(11):1493-1501, Lancet Pub Group, United Kingdom (Nov. 2017).
Techavichit, P., et al., "Secreted Frizzled-Related Protein 2 (sFRP2) Promotes Osteosarcoma Invasion and Metastatic Potential," BMC Cancer 16(1):869, BioMed Central, United Kingdom (Nov. 2016), 10 pages.
Wedekind, M.F., et al., "Immunotherapy for Osteosarcoma: Where Do We Go From Here?" Pediatric Blood & Cancer 65(9):e27227, John Wiley, United States (Sep. 2018), 9 pages.
Yamamura, S., et al., "Oncogenic Functions of Secreted Frizzled-Related Protein 2 in Human Renal Cancer," Molecular Cancer Therapeutics 9(6):1680-1687, American Association for Cancer Research Inc, United States (Jun. 2010).
International Preliminary Report on Patentability for International Application No. PCT/US2021/062854, International Search Authority, United States, mailed on May 16, 2022, 7 pages.
Bricogne, G., "Direct Phase Determination by Entropy Maximization and Likelihood Ranking: Status Report and Perspectives," Acta Crystallographica. Section D, Biological Crystallography 49(Pt1):37-60, Wiley-Blackwell, United States (Jan. 1993).
Bricogne, G., "[23] Bayesian Statistical Viewpoint on Structure Determination: Basic Concepts and Examples," Methods in Enzymology 276:361-423, Academic Press, United States (Jan. 1997).
Cockett, M.I., et al., "High Level Expression of Tissue Inhibitor of Metalloproteinases in Chinese Hamster Ovary Cells Using Glutamine Synthetase Gene Amplification," Biotechnology 8(7):662-667, Nature Publishing Company, United States (Jul. 1990).
Cunningham, B.C., and Wells, J.A., "High-resolution Epitope Mapping of hGH-receptor Interactions by Alanine-scanning Mutagenesis," Science 244(4908):1081-1085, American Association for the Advancement of Science, United States (Jun. 1989).
Foecking, M.K. and Hofstetter, H., "Powerful and Versatile Enhancer-promoter Unit for Mammalian Expression Vectors," Gene 45(1):101-105, Elsevier/North-Holland, Netherlands (1986).
Giege, R., et al., "Crystallogenesis of Biological Macromolecules: Facts and Perspectives," Acta Crystallographica. Section D, Biological Crystallography 50(Pt4):339-350, Wiley-Blackwell, United States (Jul. 1994).
Hammerling, G.J., et al., in: *Monoclonal Antibodies and T-Cell Hybridomas: Perspectives and Technical Advances*, pp. 563-681, Elsevier, New York, United States (1981).
Kabat, E.A., and Wu, T.T., "Attempts to Locate Complementarity-Determining Residues in the Variable Positions of Light and Heavy Chains," Annals of the New York Academy of Sciences 190:382-393, Blackwell, United States (Dec. 1971).
Riechmann, L., et al., "Reshaping Human Antibodies for Therapy," Nature 332:323-327, Springer Nature, United Kingdom (Mar. 1988).
Roth, W., et al., "Secreted Frizzled-related Proteins Inhibit Motility and Promote Growth of Human Malignant Glioma Cells," Oncogene 19(37):4210-4220, Nature Publishing Group, United Kingdom (Aug. 2000).
Singh, S., et al., "Impaired Wnt Signaling in Embryonal Rhabdomyosarcoma Cells From P53/c-fos Double Mutant Mice," The American Journal of Pathology 177(4):2055-2066, Elsevier, United States (Oct. 2010).
Verhoeyen, M., et al., "Reshaping Human Antibodies: Grafting an Antilysozyme Activity," Science 239(4847):1534-1536. Washington, United States (Mar. 1988).
Xiao, X., et al., "Promoting Roles of the Secreted Frizzled-Related Protein 2 as a Wnt Agonist in Lung Cancer Cells," Oncology Reports 34(5):2259-2266, Spandidos, Greece (Nov. 2015).
Office action: First examination report for 523441136 based on PCT/US2021/062854 dated May 14, 2024.
Office Action (Restriction Requirement) corresponding to U.S. Appl. No. 17/547,550 dated Apr. 26, 2023, 8 pages.
Office Action (Notice of Allowance) corresponding to U.S. Appl. No. 17/547,550 dated Aug. 22, 2023, 8 pages.
Office Action (Notice of Allowance) corresponding to U.S. Appl. No. 17/547,550 dated Nov. 6, 2023, 3 pages.
Extended European Search Report Corresponding to European Patent Application No. EP 21904485.6 dated Nov. 18, 2024, 6 Pages.

(56) References Cited

OTHER PUBLICATIONS

JP Office action (Notice of Reasons for Refusal) for Japanese Patent Application No. 2023-535346, dated Dec. 24, 2024.

FIG. 2

| Ab ID | IC50 Relative to Mo.1 |
|---|---|
| Mo.1 | 1.0 |
| Ab1 | 0.6 |
| Ab2 | 0.6 |
| Ab3 | 0.7 |
| Ab4 | 0.6 |
| Ab5 | 0.7 |
| Ab6 | 0.6 |
| Ab7 | 0.6 |
| Ab8 | 0.7 |
| Ab13 | 0.7 |
| Ab9 | 0.6 |
| Ab10 | 0.7 |
| Ab14 | 0.7 |
| Ab11 | 0.6 |
| Ab12 | 0.6 |

FIG. 4A
FIG. 4B
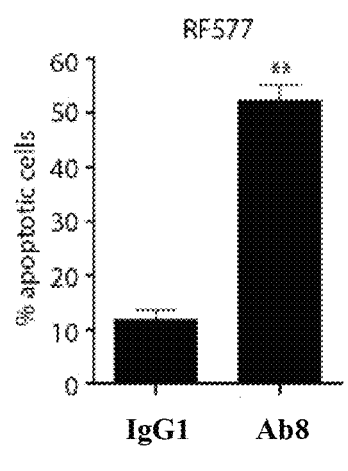
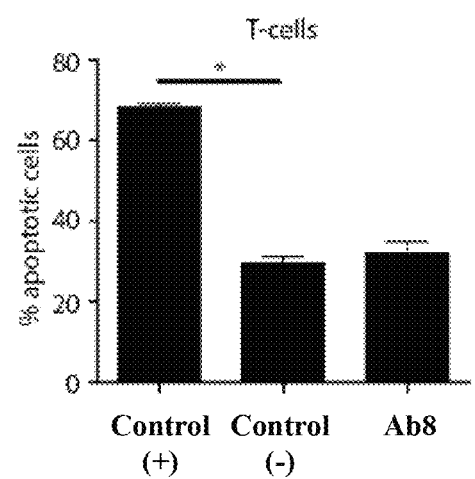

1

2

3

COMPOSITIONS AND METHODS COMPRISING SFRP2 ANTAGONISTS

1. CROSS REFERENCE TO RELATED APPLICATIONS

This application is a divisional of U.S. patent application Ser. No. 17/547,550, filed Dec. 10, 2021, hereby incorporated by reference in its entirety, which claims the priority benefit of U.S. Provisional Application No. 63/124,345, filed Dec. 11, 2020, which is hereby incorporated by reference in its entirety.

2. REFERENCE TO SEQUENCE LISTING XML

The Sequence Listing XML associated with the instant disclosure has been electronically submitted to the United States Patent and Trademark Office via the Patent Center as a 35.578 byte UTF-8-encoded xml file created on Jan. 12, 2024, and entitled "421_497_3_DIV.xml". The Sequence Listing submitted via Patent Center is hereby incorporated by reference in its entirety.

3. FIELD

The present disclosure generally relates to humanized anti-SFRP2 antibodies and antigen binding fragments thereof, compositions comprising such antibodies and antigen binding fragments thereof, methods of making and using humanized anti-SFRP2 antibodies and antigen binding fragments thereof, and methods of treating diseases, such as cancer, which methods comprise administering humanized anti-SFRP2 antibodies and antigen binding fragments thereof to a subject in need thereof, optionally as a part of a combination therapy.

4. BACKGROUND

Secreted frizzled-related protein-2 (SFRP2) has been indicated in promoting tumor growth in a number of cancers, such as breast cancer (Lee. J. L., et al., *Breast Cancer Res Treat* 84(2): 139-49 (2004); Bhati R., et al., *Am J Pathol* 172(5): 1381-90 (2008); Fontenot, E., et al., *Molecular Cancer Therapeutics* 12(5): 685-95 (2013): Lee, J. L., et al., *Breast Cancer Res Treat.* 100(1): 49-58 (2006)), angiosarcoma (Bhati, R., et al., *Am J Pathol.* 172(5): 1381-90 (2008); Fontenot, E., et al., *Molecular Cancer Therapeutics* 12(5): 685-95 (2013)), osteosarcoma (Techavichit, P., at al., *BMC Cancer* 16(1): 869 (2016)), rhabdomyosarcoma (Singh, S., et al., *The American Journal of Pathology* 177(4): 2055-66 (2010)), alveolar soft part sarcoma (Tanaka. M., et al., *Cancer Res* 77(4): 897-907 (2017)), malignant glioma (Roth, W., et al., *Oncogene* 19(37): 4210-20 (2000)), multiple myeloma (Oshima, T., et al., *Blood* 106(9): 3160-5 (2005)), renal cell carcinoma (Yamamura, S., et al. *Mol Cancer Ther* 9(6): 1680-7 (2010)), prostate cancer (Sun. Y., et al., *Oncogene* 35(33): 4321-34 (2016)), lung cancer (Xiao, X., at al., *Oncol Rep* 34(5): 2259-66 (2015)), and melanoma (Kaur, A., et al., *Nature* 532(7598): 250-4 (2016)).

Osteosarcoma (OS) is a common primary malignancy bone tumor in the pediatric population. The current standard of care consists of chemotherapy and surgical resection of the tumor. However, even with chemotherapy, only two-thirds of patients with resectable disease are cured. Long-term survival only occurs in <30% of patients with metastatic or recurrent tumors (N. C. Institute, S. Database. Ed. (2017), vol. 2017). The lung is the most common metastatic site, with approximately 80% of metastasis occurring in this anatomical location (Lindsey, B. A. et al., *Rheumatol Ther* 4: 25-43 (2017)).

Increased SFRP2 expression levels in OS patient samples correlates with poor survival, and SFRP2 overexpression suppresses normal osteoblast differentiation, promotes OS features, and facilitates angiogenesis (Kim, H., et al. *Proc Natl Acad Sci U.S.A.* 115: E11128-E11137 (2018)). Functional studies revealed stable overexpression of SFRP2 within localized human and mouse OS cells significantly increased cell migration and invasive ability in vitro and enhanced metastatic potential in vivo (Techavichit, P., et al., *BMC Cancer* 16: 869 (2016)). Additionally, knocking down SFRP2 within metastatic OS cells showed a decrease in cell migration and invasion ability in vitro, therefore corroborating a critical biological phenotype carried out by SFRP2 (Techavichit. P., et a, *BMC Cancer* 16: 869 (2016)). Thus, SFRP2 has emerged as a potential therapeutic target for osteosarcoma, however, the lack of new active agents has hindered any progress in increasing survival for over three decades, and, as such, novel treatment approaches are severely needed (Wedekind, M. F., et al, *Pediatr Blood Cancer* 65: e27227 (2018)).

Furthermore, expression of PD-L1 in osteosarcoma correlates with immune cell infiltration and has been found to be significantly associated with poor five-year-event-free-survival (EFS) (Koirala, P., et al., *Sci Rep* 6: 30093 (2016)). Despite these findings, there was lack of efficacy in treatment of osteosarcoma in a phase II trial of pembrolizumab (SARC028), where only 5% of patients with metastatic osteosarcoma had an objective response (Tawbi, H. A., et al., *Lancet Oncol* 18: 1493-1501 (2017)). These findings further indicate the pressing need for new treatments of osteosarcoma.

5. BRIEF SUMMARY

The present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide at least 90%, 95%, or 99% identical to a polypeptide comprising the amino acid sequence of SEQ ID NO: 1, 2, 3, or 4; and further wherein said antibody or antigen binding fragment thereof comprises a variable light (VL) chain polypeptide at least 90%, 95%, or 99% identical to a polypeptide comprising the amino acid sequence of SEQ ID NO: 5, 6, 7, 8, or 9.

Furthermore, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 1 and SEQ ID NO: 6, respectively (Ab1).

Moreover, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 1 and SEQ ID NO: 7, respectively (Ab2).

Furthermore, the present disclosure generally relates to a humanized anti-secreted frizzled-related protein 2 (SFRP2)

antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 1 and SEQ ID NO: 8, respectively (Ab3).

Moreover, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 1 and SEQ ID NO: 9, respectively (Ab4).

Furthermore, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 2 and SEQ ID NO: 6, respectively (Ab5).

Moreover, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 2 and SEQ ID NO: 7, respectively (Ab6).

Furthermore, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 2 and SEQ ID NO: 8, respectively (Ab7).

Moreover, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 2 and SEQ ID NO: 9, respectively (Ab8).

In some aspects, provided herein is a humanized anti-secreted frizzled-related protein 2 (SFRP2) antibody or antigen binding fragment thereof, which binds SFRP2, wherein said antibody or antigen binding fragment thereof comprises a complementary determining region (CDR) H1 comprising the amino acid sequence of SEQ ID NO:19, a CDR 112 comprising the amino acid sequence of SEQ ID NO:20, a CDR H3 comprising the amino acid sequence of SEQ ID NO:21, a CDR L1 comprising the amino acid sequence of SEQ ID NO:22, a CDR L2 comprising the amino acid sequence of SEQ ID NO:23, and a CDR L3 comprising the amino acid sequence of SEQ ID NO:24 (Ab8).

In some aspects, provided herein is a humanized anti-secreted frizzled-related protein 2 (SFRP2) antibody or antigen binding fragment thereof which binds SFRP2, wherein said antibody or antigen binding fragment thereof comprises a heavy chain polypeptide and a light chain polypeptide comprising the amino acid sequences of SEQ ID NO: 15 and SEQ ID NO: 16, respectively (Ab8).

Furthermore, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 3 and SEQ ID NO: 6, respectively (Ab9).

Moreover, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 3 and SEQ ID NO: 7, respectively (Ab10).

Furthermore, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 4 and SEQ ID NO: 8, respectively (Ab11).

Moreover, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 4 and SEQ ID NO: 9, respectively (Ab12).

Furthermore, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 3 and SEQ ID NO: 5, respectively (Ab13).

Moreover, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 3 and SEQ ID NO: 9, respectively (Ab14).

Furthermore, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 1 and SEQ ID NO: 5, respectively (Ab15).

Moreover, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 2 and SEQ ID NO: 5, respectively (Ab16).

Furthermore, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 4 and SEQ ID NO: 5, respectively (Ab17).

Moreover, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 3 and SEQ ID NO: 8, respectively (Ab18).

Furthermore, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 4 and SEQ ID NO: 6, respectively (Ab19).

Moreover, the present disclosure generally relates to a humanized anti-secreted frizzled-related protein 2 (SFRP2) antibody or antigen binding fragment thereof which binds SFRP2, wherein said antibody or antigen binding fragment thereof comprises a variable heavy (VH) chain polypeptide and a variable light (VL) chain polypeptide comprising the amino acid sequences of SEQ ID NO: 4 and SEQ ID NO: 7, respectively (Ab20).

Furthermore, the present disclosure generally relates to a humanized anti-secreted frizzled-related protein 2 (SFRP2) antibody or antigen binding fragment thereof which binds SFRP2, wherein the antibody or antigen binding fragment thereof comprises a VH chain polypeptide and VL chain polypeptide comprising the amino acid sequences of: i. SEQ ID NO: 1 and SEQ ID NO: 6, respectively (Ab1); ii. SEQ ID NO: 1 and SEQ ID NO: 7, respectively (Ab2); iii. SEQ ID NO: 1 and SEQ ID NO: 8, respectively (Ab3); iv. SEQ ID NO: 1 and SEQ ID NO: 9, respectively (Ab4); v. SEQ ID NO: 2 and SEQ ID NO: 6, respectively (Ab5): vi. SEQ ID NO: 2 and SEQ ID NO: 7, respectively (Ab6): vii. SEQ ID NO: 2 and SEQ ID NO: 8, respectively (Ab7); viii. SEQ ID NO: 2 and SEQ ID NO: 9, respectively (Ab8); ix. SEQ ID NO: 3 and SEQ ID NO: 6, respectively (Ab9); x. SEQ ID NO: 3 and SEQ ID NO: 7, respectively (Ab10); xi. SEQ ID NO: 4 and SEQ ID NO: 8, respectively (Ab11); xii. SEQ ID NO: 4 and SEQ ID NO: 9, respectively (Ab12); xiii. SEQ ID NO: 3 and SEQ ID NO: 5, respectively (Ab13); xiv. SEQ ID NO: 3 and SEQ ID NO: 9, respectively (Ab14); xv. SEQ ID NO: 1 and SEQ ID NO: 5, respectively (Ab15); xvi. SEQ ID NO: 2 and SEQ ID NO: 5, respectively (Ab16); xvii. SEQ ID NO: 4 and SEQ ID NO: 5, respectively (Ab17); xviii. SEQ ID NO: 3 and SEQ ID NO: 8, respectively (Ab18); xix. SEQ ID NO: 4 and SEQ ID NO: 6, respectively (Ab19): or xx. SEQ ID NO: 4 and SEQ ID NO: 7, respectively (Ab20).

In some aspects, the antibody or antigen-binding fragment comprises a heavy chain constant region and a light chain constant region. In some aspects, the antibody or antigen-binding fragment is a monoclonal antibody. In some aspects, the antibody is a full-length antibody. In some aspects, the antibody or antigen binding fragment is an antigen binding fragment.

In some aspects, the antibody or antigen binding fragment thereof comprises an IC50 value of 0.7 or less, 0.6 or less, or 0.5 or less relative to the IC50 value of an antibody or antigen binding fragment thereof comprising a VH chain polypeptide and VL chain polypeptide of SEQ ID NOs: 10 and 11, respectively (Mo.1), wherein the IC50 values are measured by an ELISA assay.

Moreover, the present disclosure generally relates to an isolated polynucleotide comprising a nucleic acid molecule encoding the heavy chain variable region or heavy chain of an antibody or antigen-binding fragment thereof of an antibody or antigen binding fragment as discussed herein. In some aspects, the nucleic acid molecule encodes the VH of SEQ ID NO: 1, 2, 3, or 4.

Furthermore, the present disclosure generally relates to an isolated polynucleotide comprising a nucleic acid molecule encoding the light chain variable region or light chain of the antibody or antigen-binding fragment thereof of an antibody or antigen binding fragment as discussed herein. In some aspects, the nucleic acid molecule encodes the VL of SEQ ID NO: 5, 6, 7, 8, or 9.

Moreover, the present disclosure generally relates to an isolated polynucleotide comprising a nucleic acid molecule encoding the heavy chain variable region or heavy chain of the antibody or antigen-binding fragment thereof of an antibody or antigen binding fragment as discussed herein and the light chain variable region or light chain of the antibody or antigen-binding fragment thereof of an antibody or antigen binding fragment as discussed herein.

Furthermore, the present disclosure generally relates to an isolated vector comprising a polynucleotide as discussed herein, e.g., isolated polynucleotide comprising a nucleic acid molecule encoding the heavy chain variable region or heavy chain of the antibody or antigen-binding fragment thereof of an antibody or antigen binding fragment as discussed herein: e.g., the light chain variable region or light chain of the antibody or antigen-binding fragment thereof of an antibody or antigen binding fragment as discussed herein.

Moreover, the present disclosure generally relates to a host cell comprising (a) the polynucleotide as discussed herein, (b) a vector as discussed herein, or (c) a first vector comprising a nucleic acid molecule encoding the heavy chain variable region or heavy chain of the antibody or antigen-binding fragment thereof of an antibody or antigen binding fragment as discussed herein and a second vector comprising a nucleic acid molecule encoding the light chain variable region or light chain of the antibody or antigen-binding fragment thereof of an antibody or antigen binding fragment as discussed herein. In some aspects, the host cell is selected from the group consisting of *E. coli, Pseudomonas, Bacillus, Streptomyces*, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, and human cell in tissue culture. In some aspects, the host cell is a CHO cell.

Furthermore, the present disclosure generally relates to a method of producing an antibody or antigen-binding fragment thereof that binds to SFRP2 comprising culturing the a host cell as discussed herein so that the nucleic acid molecule is expressed and the antibody or antigen-binding fragment thereof is produced, optionally wherein the method further comprises isolating the antibody or antigen-binding fragment thereof from the culture. In some aspects, the isolated antibody or antigen-binding fragment thereof is substantially free of precipitates. In some aspects, the isolated antibody or antigen-binding fragment thereof comprises a humanized antibody.

Moreover, the present disclosure generally relates to an isolated antibody or antigen-binding fragment thereof that specifically binds to secreted frizzled related protein 2 (SFRP2) and is encoded by a polynucleotide as described herein or produced by a method as described herein.

Furthermore, the present disclosure generally relates to a pharmaceutical composition comprising a therapeutically effective amount of an antibody or antigen-binding fragment thereof as discussed herein and a pharmaceutically acceptable excipient.

Moreover, the present disclosure generally relates to a method of treating cancer in a patient, the method comprising administering to the patient a pharmaceutical composition as discussed herein. In some aspects, the cancer is a breast cancer, a malignant glioma, a multiple myeloma, a renal cell carcinoma, a kidney cancer, a prostate cancer, a lung cancer, a melanoma, a non-small cell lung cancer, a pancreatic cancer, a colorectal cancer, a bladder cancer, a hepatocellular carcinoma, a gastrointestinal cancer, and a sarcoma including, but not limited to an angiosarcoma, an osteosarcoma, a rhabdomyosarcoma, and an alveolar soft part sarcoma. In some aspects, the cancer is osteosarcoma. In some aspects, the method of treating cancer in a patient further comprises administering an antagonist of an inhibitory immune checkpoint molecule, optionally wherein the immune checkpoint molecule is PD-1. In some aspects, the antagonist of PD-1 is an anti-PD-1 antibody or antigen-binding fragment thereof, optionally wherein the anti-PD-1 antibody or antigen-binding fragment thereof is selected from the group consisting of nivolumab, pembrolizumab, MEDI-0680 (AMP-514), camrelizumab (SHR-1210), tislelizumab (BGB-A317), and spartalizumab (NPVPDR001, NVS240118, PDR001).

6. BRIEF DESCRIPTION OF THE DRAWINGS

FIG. 1A presents an image of a Coomassie Blue-stained SDS-PAGE gel of various different purified humanized anti-SFRP2 antibodies in accordance with Example 1. The lanes of the SDS-PAGE gel were loaded as follows: 1=MW marker; 2=Ab1; 3=Ab2; 4=Ab3; 5=Ab4; 6=Ab5; 7=Ab6; 8=Ab7; 9=Ab8; 10=Ab9; 11=MW marker; 12=MW marker; 13=Ab10; 14=Ab1; 15=Ab12; 16=MW marker; 17=Ab13; and Lane 18=Ab14.

Figure 1B:
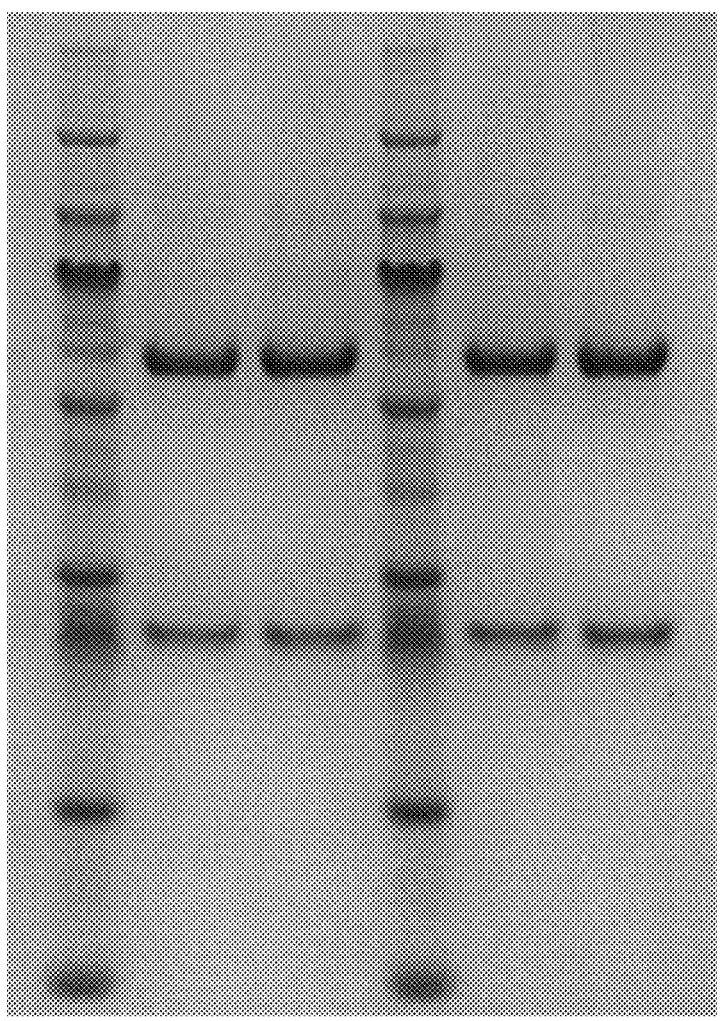

FIG. 1B presents an image of a Coomassie Blue-stained SDS-PAGE gel of various different purified chimeric antibodies in accordance with Example 1. The lanes of the SDS-PAGE gel were loaded as follows: 1=MW marker; 2=Chi.1 purified from HEK cells: 3=Chi.2 purified from HEK cells; 4=MW marker: 5=Chi.1 purified from NS0 cells; 6=Chi.2 purified from NS0 cells.

FIG. 2 presents a table of relative IC50 values of various different humanized anti-SFRP2 antibodies in accordance with Example 2. The relative $IC_{50}$ value for each antibody was calculated by dividing the IC50 value for the test antibody by that of antibody Mo.1 assayed on the same ELISA plate.

Figure 3:
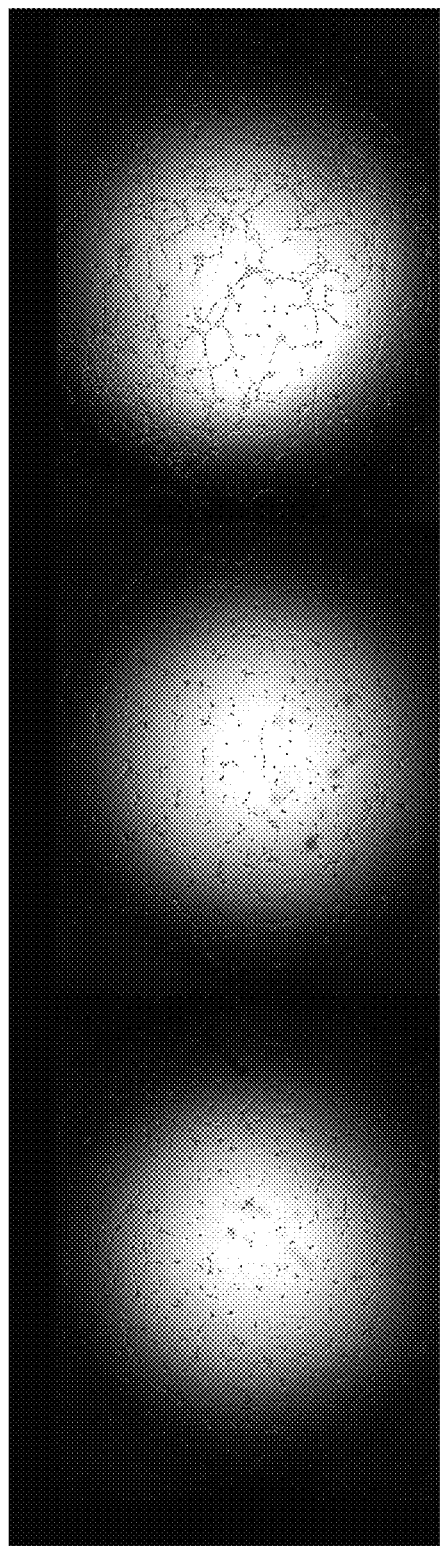

FIG. 3 presents images of endothelial tube formation assays taken in accordance with Example 2. In FIG. 3: 1=control; 2=treatment with Ab8: and 3=treatment with Ab11.

FIG. 4A-FIG. 4B present graphical representations of cell-based assays performed in accordance with Example 3. FIG. 4A presents a graphical representation of an assay in which an osteosarcoma model cell line (RF577 cell line) was treated with either IgG1 (control) or Ab8. FIG. 4B presents a graphical representation of an T-cell apoptosis assay in which T-cells were treated with Ab8 and further presents positive and negative controls.

Figure 5:
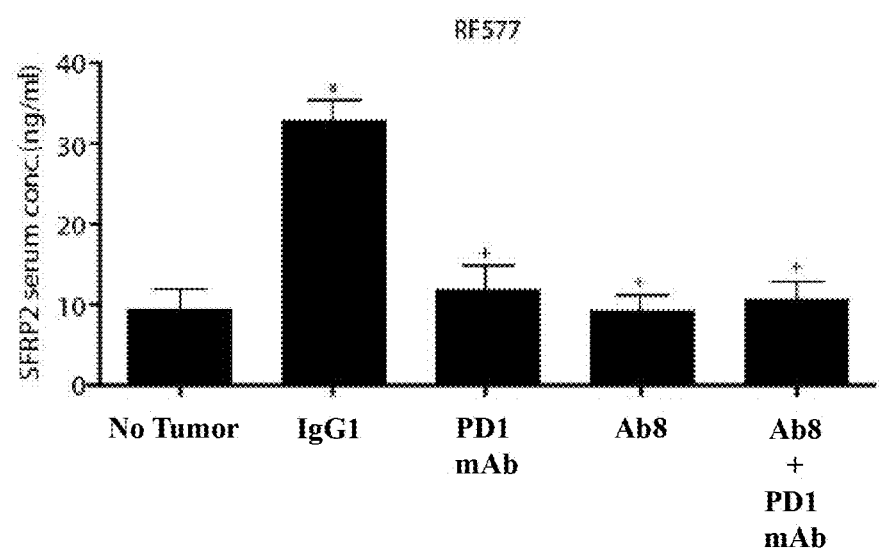

FIG. 5 presents a graphical representation of the SFRP2 serum levels of various different mice administered various different treatments in accordance with Example 4. The SFRP2 level of a mouse with no tumor, and the SFRP2 levels of mice with metastatic osteosarcoma that were treated with either IgG1, PD-1 mAb alone, Ab8 alone, or a combination of Ab8 and PD-1 mAb are presented. The X-axis represents the treatment administered, and the Y-axis represents the SFRP2 serum concentration (ng/ml).

Figure 6:
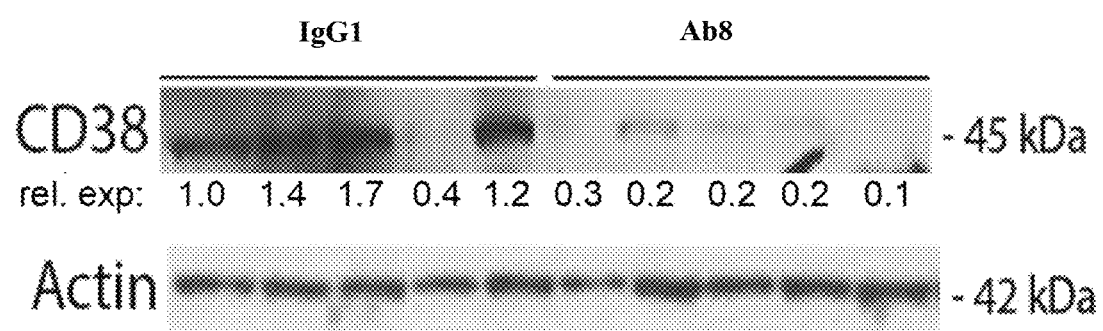

FIG. 6 presents images of Western blots which measured CD38 levels in accordance with Example 5. Splenocytes of mice with metastatic osteosarcoma were treated with either IgG1 or Ab8, and Western blot analysis was subsequently performed in accordance with Example 5. Actin was used for normalization.

Figure 7A:
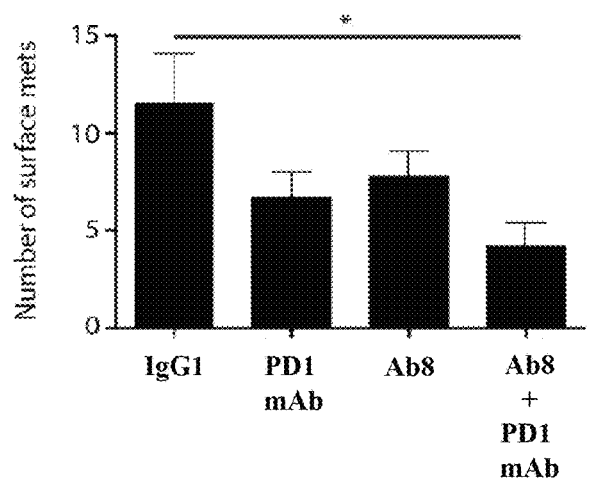
Figure 7B:
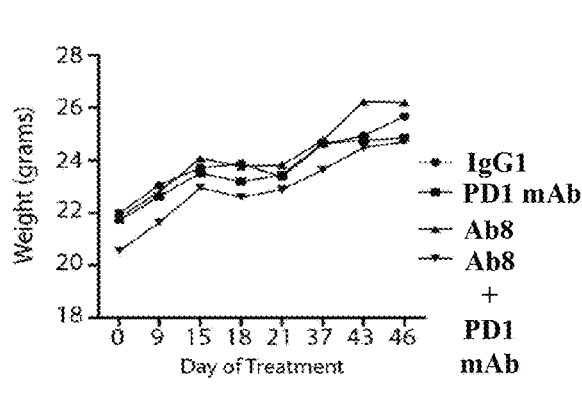

FIG. 7A-FIG. 7B present graphical representations of data related to the treatment of metastatic osteosarcoma growth in accordance with Example 6. FIG. 7A presents a graphical representation a metastatic RF577 osteosarcoma in vivo experiment performed in accordance with Example 6. The X-axis represents the treatment used, and the Y-axis represents the number of lung surface metastases observed. FIG. 7B presents a graphical representation of a toxicity study that was performed in accordance with Example 6. The X-axis represents the week of treatment of the mouse, and the Y-axis represents the weight of the mouse. The closed circles represent IgG1; the closed squares represent PD1 mAb; the triangles represent Ab8; and the inverted triangles represent a combination treatment of Ab8 and PD1 mAb.

Figure 8:
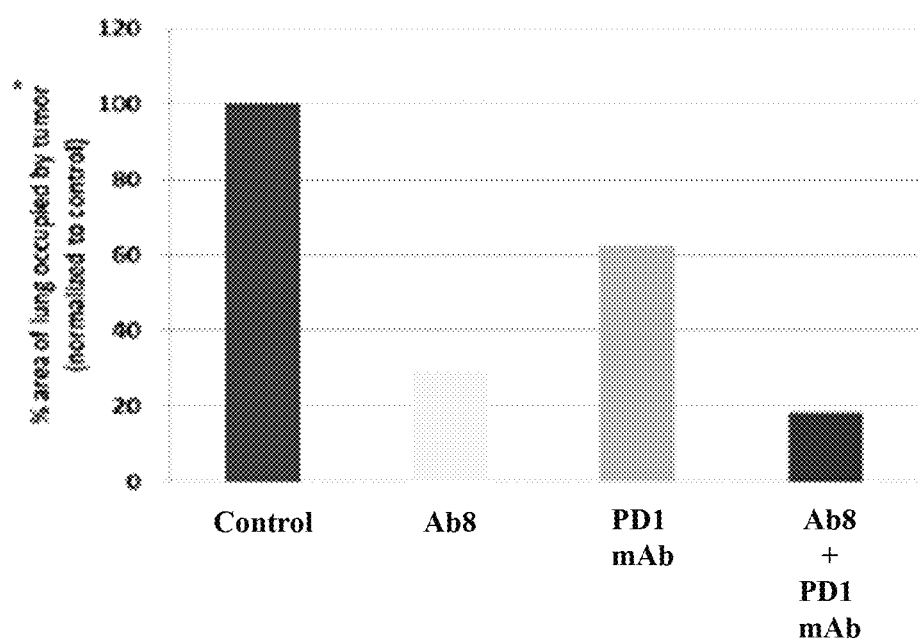

FIG. 8 presents a graphical representation of data related to the treatment of metastatic osteosarcoma growth in accordance with Example 6. The X-axis represents the treatment used, and the Y-axis represents the percent area of lung occupied by tumor observed. The percent of lung occupied by tumor was calculated by dividing the tumor area by normal lung area multiplied by 100. The treatments were normalized to the control.

Figure 9A:
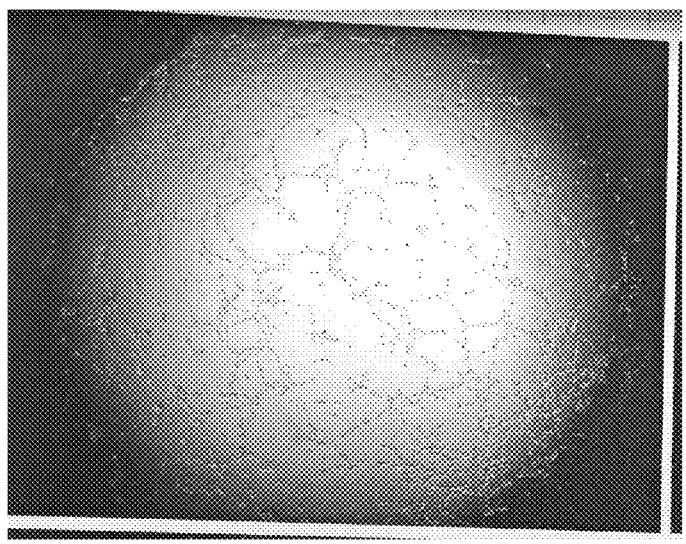
Figure 9A:
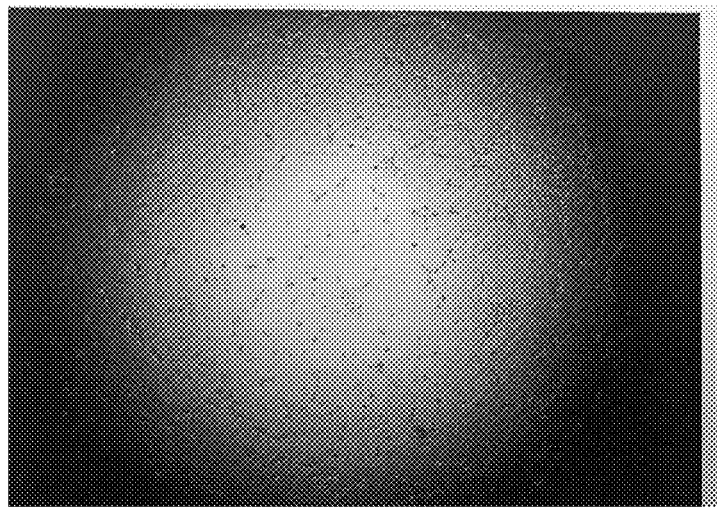
Figure 9A:
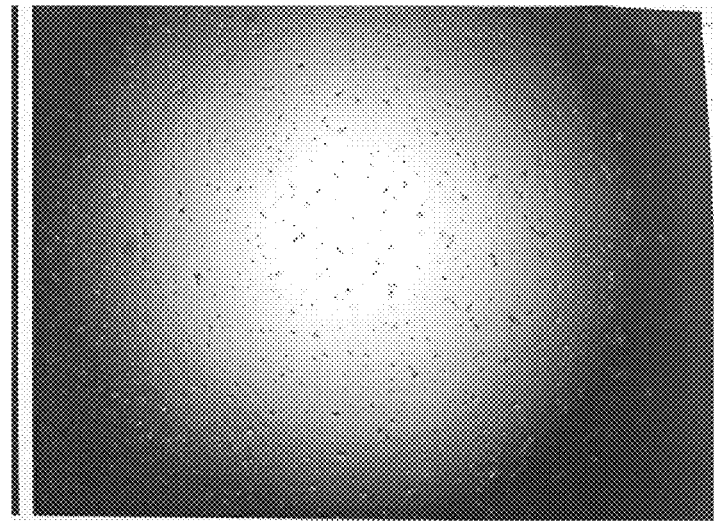
Figure 9B:
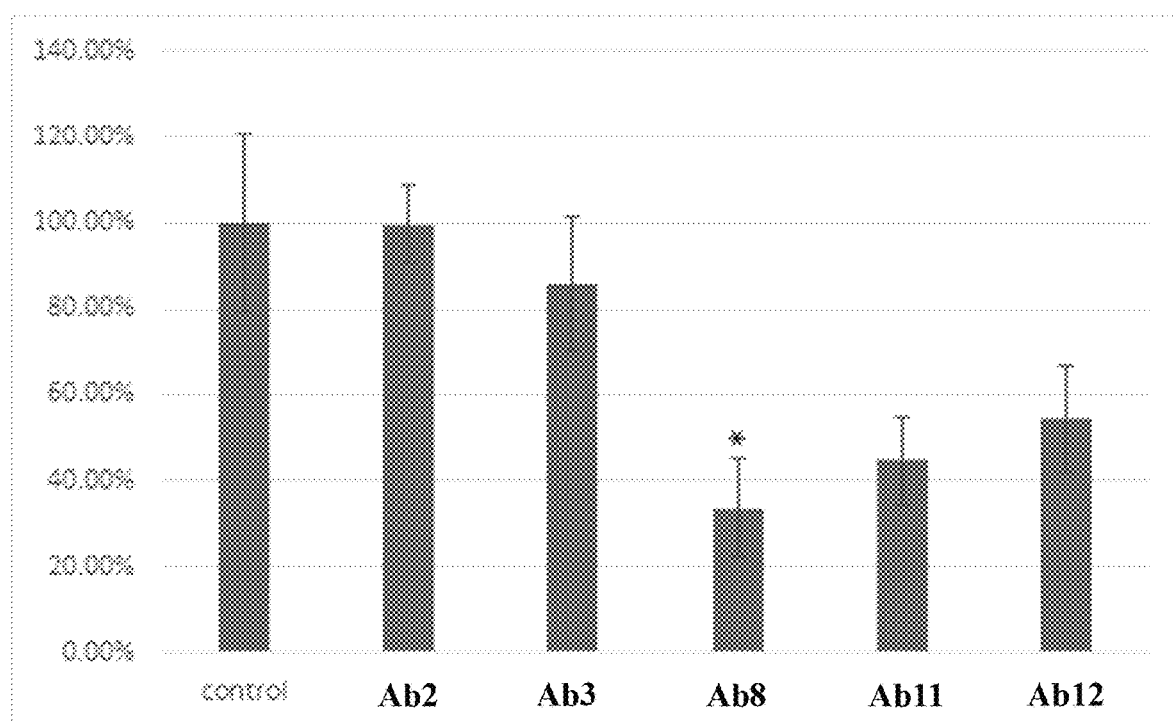

FIG. 9A-FIG. 9B present images of endothelial tube formation assays (FIG. 9A) and a graphical representation of the results of endothelial tube formation assays (FIG. 9B) in accordance with Example 2. In FIG. 9A, 1=Control; 2=Ab11; and 3=Ab8. FIG. 9B presents a graphical representation of the tube branch points relative to control (#branch points in treated/#branch points in control) as demonstrated by each antibody in the tube formation assay in accordance with Example 2. A lower percentage indicates stronger inhibition of endothelial tube formation.

Figure 10:
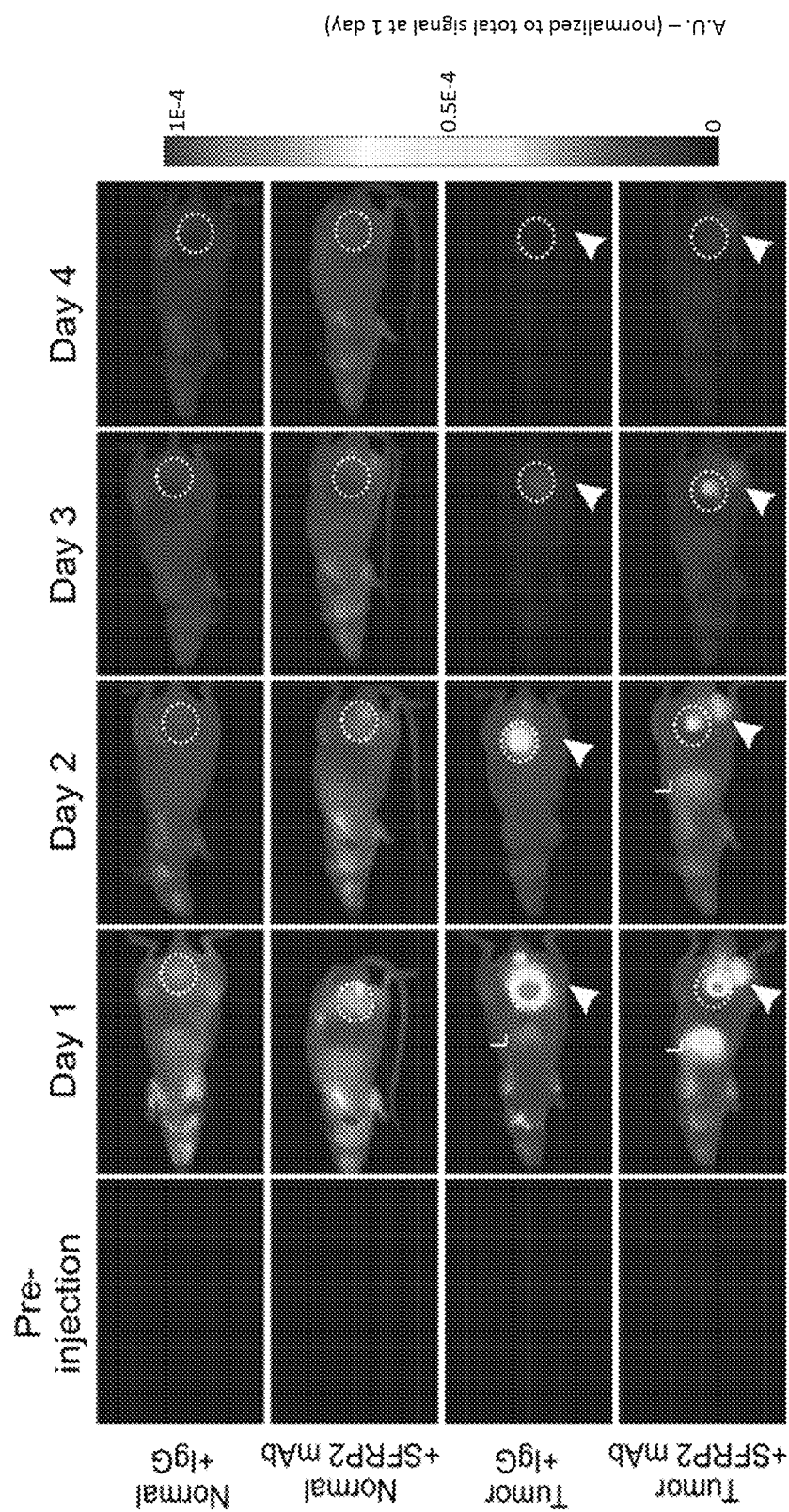

FIG. 10 presents images of the biodistribution of IgG1 and hSFRP2 mAB in mice after tail vein injection of treatment with fluorophore-tagged nanoparticles into control and breast-cancer model mice. Arrows point to tumor.

Figure 11A:
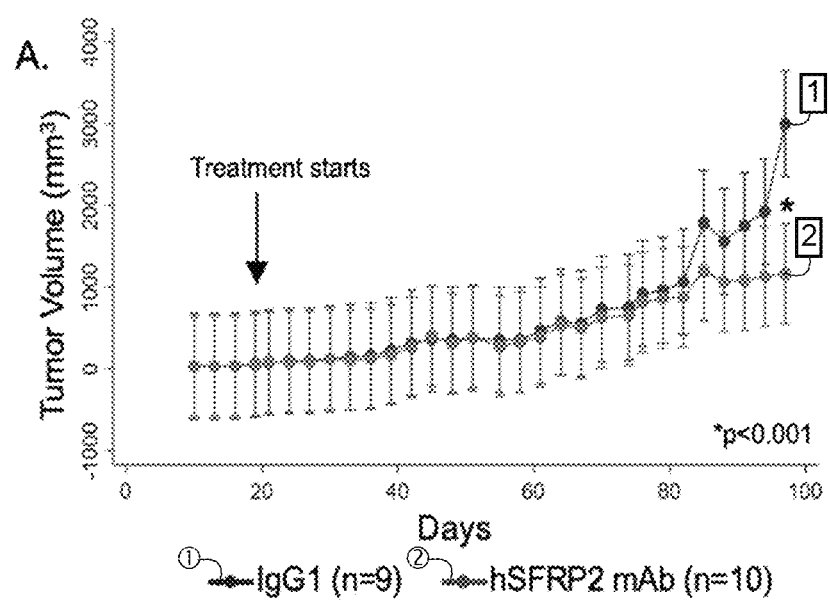
Figure 11B:
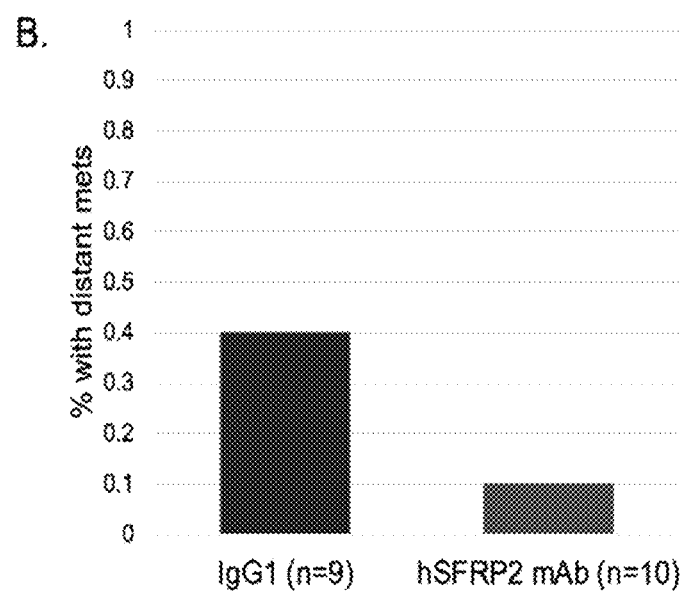
Figure 11C:
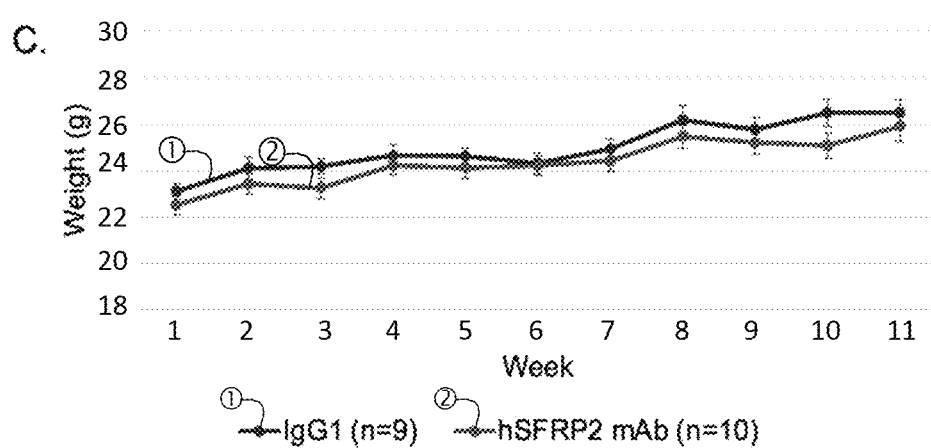

FIG. 11A-11C present graphical representations of n vivo tumor inhibition studies using hSFRP2mAB. FIG. 11A presents tumor volume (mm$^3$) over a 97 day period in response to treatment with hSFRP2 mAB or IgG1 beginning on day 19. FIG. 11B presents the percentage of animals in the study that had distant metastases after a 97 day period in response to treatment with hSFRP2 mAB or IgG1. FIG. 11C presents the weights of the hSFRP2 mAB treated and IgG1 treated animals as measured weekly over the 97 day period.

7. DETAILED DESCRIPTION

Provided herein are humanized antibodies and antigen binding fragments thereof that bind SFRP2. In some aspects, the humanized anti-SFRP2 antibodies and antigen binding fragments thereof provided herein are used for the treatment of diseases associated with increased SFRP2 expression levels, such as various different cancers, e.g., osteosarcoma. Humanized anti-SFRP2 antibodies and antigen binding fragments thereof can, for example, selectively induce apoptosis of SFRP2-expressing osteosarcoma cells and/or other tumor cells e.g., the humanized anti-SFRP2 antibodies do not induce apoptosis in T-cells but do induce apoptosis of osteosarcoma cells and/or other tumor cells; reduce the amount of SFRP2 in a cell; reduce the serum level of SFRP2 in a treated subject; reduce the metastatic tumor growth in osteosarcoma and/or other tumor types in a subject; reduce the amount of osteosarcoma lung metastases in a patient, and/or reduce the amount of CD38 protein in a patient. These activities of humanized anti-SFRP2 antibodies and antigen binding fragments thereof may promote effective treatment of diseases in which SFRP2 is overexpressed and/or wherein SFRP2 expression or overexpression is associated with a diseased state, such as various different cancers, e.g., osteosarcoma.

Also provided herein are isolated nucleic acids (polynucleotides), such as complementary DNA (cDNA), encoding such humanized antibodies and antigen-binding fragments thereof. Further provided are vectors (e.g., expression vectors) and cells (e.g., host cells) comprising nucleic acids (polynucleotides) encoding such humanized antibodies and antigen-binding fragments thereof. Also provided are methods of making such humanized antibodies and antigen-binding fragments thereof.

In other aspects, provided herein are methods for using such humanized antibodies and antigen binding fragments thereof, for example, to modulate SFRP2 activity. SFRP2 activity can be modulated, for example, by binding of the humanized antibodies and antigen binding fragments described herein to SFRP2. Modulation of SFRP2 activity by the antibodies and antigen fragments described herein may result in reduction of the amount of SFRP2 in a cell; reduction of the serum level of SFRP2 in a treated subject; reduction of the metastatic osteosarcoma growth in a subject; reduction of the amount of osteosarcoma hung metastases in a patient; selective induction of apoptosis of an osteosarcoma cell, e.g., the humanized anti-SFRP2 antibodies do not induce apoptosis in T-cells but do induce apoptosis of osteosarcoma cells: and/or reduction of the amount of CD38 protein in a subject.

In further aspects, humanized anti-SFRP2 antibodies and antigen binding fragments thereof provided herein are used to treat a disease, such as a cancer, e.g., osteosarcoma. In some aspects, treatment comprises administering an effective amount of one or more humanized anti-SFRP2 antibodies and antigen binding fragments thereof as described herein to a subject in need thereof. In some aspects, such diseases include, but are not limited to, cancer, such as, for example, a breast cancer, a malignant glioma, a multiple myeloma, a renal cell carcinoma, a kidney cancer, a prostate cancer, a lung cancer, a melanoma, a non-small cell lung cancer, a pancreatic cancer, a colorectal cancer, a bladder cancer, a hepatocellular carcinoma, a gastrointestinal cancer, and a sarcoma including, but not limited to an angiosarcoma, an osteosarcoma, a rhabdomyosarcoma, and an alveolar soft part sarcoma. In some aspects, such diseases include those in which increased expression of SFRP2, overexpression of SFRP2, and/or expression levels of SFRP2 associated with a diseased state occurs, e.g., a breast cancer, a malignant glioma, a multiple myeloma, a renal cell carcinoma, a kidney cancer, a prostate cancer, a lung cancer, a melanoma, a non-small cell lung cancer, a pancreatic cancer, a colorectal cancer, a bladder cancer, a hepatocellular carcinoma, a gastrointestinal cancer, and a sarcoma including, but not limited to an angiosarcoma, an osteosarcoma, a rhabdomyosarcoma, and an alveolar soft part sarcoma.

6.1 Terminology

As used herein, the term "SFRP2" refers to secreted-frizzled related protein 2 polypeptides including, but not limited to, native SFRP2 polypeptides and any naturally occurring variants thereof. As used herein, the term "human SFRP2" refers to a polypeptide comprising the amino acid sequence of SEQ ID NO: 12. An "SFRP2 polynucleotide," "SFRP2 nucleotide," or "SFRP2 nucleic acid" refers to a polynucleotide encoding any SFRP2, including those described above.

The term "antibody" means an immuoglobulin molecule that recognizes and specifically binds to a target, such as a protein, polypeptide, peptide, carbohydrate, polynucleotide, lipid, or combinations of the foregoing (e.g., a glycoprotein), through at least one antigen recognition site within the variable region of the immunoglobulin molecule. As used herein, the term "antibody" encompasses polyclonal antibodies, monoclonal antibodies, chimeric antibodies, humanized antibodies, human antibodies, and any other immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked, part of a fusion protein, or conjugated to other molecules such as toxins, radioisotopes, etc.

The term "antibody fragment" refers to a portion of an antibody. An "antigen-binding fragment," "antigen-binding domain," or "antigen-binding region." refers to a portion of an antibody that binds to an antigen. An antigen-binding fragment can contain the antigenic determining regions of an antibody (e.g., the complementarity determining regions (CDR)). An antigen-binding fragment can contain some or all of the VH and/or VL chain polypeptides of an antibody. Examples of antigen-binding fragments of antibodies include, but are not limited to Fab, Fab', F(ab')2, and Fv fragments, linear antibodies, and single chain antibodies. An antigen-binding fragment of an antibody can be derived from any animal species, such as rodents (e.g., mouse, rat, or hamster) and humans or can be artificially produced.

The terms "anti-SFRP2 antibody," "SFRP2 antibody" and "antibody that binds to SFRP2" refer to an antibody that is capable of binding SFRP2 with sufficient affinity such that the antibody is useful as a diagnostic, a therapeutic, and/or as a modulator of SFRP2 activity.

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, a "monoclonal" antibody or antigen-binding fragment thereof refers to such antibodies and antigen-binding fragments thereof made in any number of manners including but not limited to by hybridoma, phage selection, recombinant expression, and transgenic animals.

As used herein, the terms "variable region" or "variable domain" are used interchangeably and are common in the alt. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen.

The terms "VL" and "VL domain" are used interchangeably to refer to the light chain variable region of an antibody.

The terms "VH" and "VH domain" are used interchangeably to refer to the heavy chain variable region of an antibody.

The "hypervariable regions" in each chain are held together in close proximity by FRs, and with the hypervariable regions from the other chain, contribute to the formation of the antigen-binding site of antibodies (see Kabat et al. Sequences of Proteins of Immunological Interest, 1992; Chothia et al., Conformations of immuoglobulin hypervariable regions, *Nature* (1989) 342:877-83.). The term "hypervariable region" as used herein refers to the amino acid residues of an antibody, which are responsible for antigen binding. The hypervariable region generally comprises amino acid residues from a "complementary determining region" or "CDR", the latter being of highest sequence variability and/or involved in antigen recognition.

The term "Kabat numbering" and like terms are recognized in the art and refer to a system of numbering amino acid residues in the heavy and light chain variable regions of an antibody or an antigen-binding fragment thereof (sec, e.g., Kabat E A & Wu T T (1971) Ann NY Acad Sci 190: 382-391 and Kabat E A et al., (1991) Sequences of Proteins of Immunological Interest. Fifth Edition, U.S. Department of Health and Human Services. NIH Publication No. 91-3242).

As used herein, the term "constant region" or "constant domain" are interchangeable and have the meaning common in the art. The constant region is an antibody portion, e.g., a carboxyl terminal portion of a light and or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain. In certain aspects, an antibody or antigen-binding fragment comprises a constant region or portion thereof that is sufficient for antibody-dependent cell-mediated cytotoxicity (ADCC).

As used herein, the term "heavy chain" when used in reference to an antibody can refer to any distinct type, e.g., alpha ($\alpha$), delta ($\delta$), epsilon ($\epsilon$), gamma ($\gamma$), and mu ($\mu$), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and IgG4. Heavy chain amino acid sequences are well known in the art. In some aspects, the heavy chain is a human heavy chain.

As used herein, the term "light chain" when used in reference to an antibody can refer to any distinct type, e.g., kappa ($\kappa$) or lambda ($\lambda$) based on the amino acid sequence of the constant domains. Light chain amino acid sequences are well known in the art. In some aspects, the light chain is a human light chain.

The term "chimeric" antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g. mouse, rat, rabbit, etc.) with the desired specificity, affinity, and capability while the constant regions are homologous to the sequences in antibodies or antigen-binding fragments thereof derived from another (usually human) to avoid eliciting an immune response in that species.

The term "humanized" antibody or antigen-binding fragment thereof refers to forms of non-human (e.g. murine) antibodies or antigen-binding fragments that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the complementarity determining regions (CDRs) are replaced by residues from the CDRs of a non-human species (e.g. mouse, rat, rabbit, hamster) that have the desired specificity, affinity, and capability ("CDR grafted")(Jones et al., Nature 321:522-525 (1986); Riechmann et al., Nature 332:323-327 (1988): Verhoeyen et al., Science 239:1534-1536 (1988)). The humanized antibody or antigen-binding fragment thereof can be further modified by the substitution of additional residues either in the Fv framework region and/or within the replaced non-human residues to refine and optimize the specificity, affinity, and/or capability of the antibody or antigen-binding fragment thereof. In general, the humanized antibody or antigen-binding fragment thereof will comprise VH and VL that comprise substantially all of at least one, and typically two or three, of the CDR regions that correspond to the non-human immunoglobulin, whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., Proc. Nat. Acad. Sci., USA, 91(3):969-973 (1994), and Roguska et al., Protein Eng. 9(10):895-904 (1996). In some aspects, a "humanized antibody" is a resurfaced antibody.

"Binding affinity" generally refers to the strength of the sum total of non-covalent interactions between a single binding site of a molecule (e.g., an antibody or antigen-binding fragment thereof) and its binding partner (e.g., an antigen). Unless indicated otherwise, as used herein, "binding affinity" refers to intrinsic binding affinity which reflects a 1:1 interaction between members of a binding pair (e.g., antibody or antigen-binding fragment thereof and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody or antigen-binding fragment thereof to an antigen, and $k_{off}$ refers to the dissociation rate constant of, e.g., an antibody or antigen-binding fragment thereof from an antigen. The $k_{on}$ and $k_{off}$ can be determined by techniques known to one of ordinary skill in the art, such as BIAcore® or KinExA.

As used herein, the terms "immunospecifically binds," "immunospecifically recognizes," "specifically binds," and "specifically recognizes" are analogous terms in the context of antibodies or antigen-binding fragments thereof. These terms indicate that the antibody or antigen-binding fragment thereof binds to an epitope via its antigen-binding domain and that the binding entails complementarity between the antigen binding domain and the epitope. Accordingly, an antibody that "specifically binds" to human SFRP2 (e.g., SEQ ID NO: 12) may also bind to SFRP2 from other species and/or SFRP2 proteins produced from other human alleles.

A antibody that is "blocking" or that "blocks" or that is "inhibitory" or that "inhibits" is an antibody that reduces or inhibits (partially or completely) binding of its target protein to one or more ligands when the antibody is bound to the target protein, and/or that reduces or inhibits (partially or completely) one or more activities or functions of the target protein when the antibody is bound to the target protein.

As used herein, an "epitope" is a term in the art and refers to a localized region of an antigen to which an antibody or antigen-binding fragment thereof can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In some aspects, the epitope to which an antibody or antigen-binding fragment thereof binds can be determined by, e.g., NMR spectroscopy, X-ray diffraction crystallography studies. ELISA assays, hydrogen/deuterium exchange coupled with mass spectrometry (e.g., liquid chromatography electrospray mass spectrometry), array-based oligopeptide scanning assays, and/or mutagenesis mapping (e.g., alanine scanning or other site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23: Chayen N E (1997) Structure 5: 1269-1274: McPherson A (1976) J Biol Chem 251: 6300-6303). Crystals of an antibody or antigen-binding fragment thereof and its antigen can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al., U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies can be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

An antibody is said to "competitively inhibit" binding of a reference antibody to a given epitope if it preferentially binds to that epitope or an overlapping epitope such that it blocks, to some degree, binding of the reference antibody to the epitope. Competitive inhibition may be determined by any method known in the art, for example, competition ELISA assays.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some aspects, an antibody, polynucleotide, vector, cell, or composition which is isolated is substantially pure.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this disclosure are based upon antibodies, in some aspects, the polypeptides can occur as single chains or associated chains.

As used herein, the term "host cell" can be any type of cell, e.g., a primary cell, a cell in culture, or a cell from a cell line. In some aspects, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome.

As used herein, the term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The terms "administer," "administering," "administration," and the like, as used herein, refer to methods that may be used to deliver a drug, e.g., a humanized anti-SFRP2 antibody or antigen-binding fragment thereof, to the desired site of biological action. Administration techniques that can be employed with the agents and methods described herein are found in e.g., Goodman and Gilman, *The Pharmacological Basis of Therapeutics*, current edition, Pergamon; and Remington's, *Pharmaceutical Sciences*, current edition, Mack Publishing Co., Easton, Pa.

As used herein, the terms "subject" and "patient" are used interchangeably. The subject can be a mammal such as a non-human animal (e.g., cow, pig, horse, cat, dog, rat, mouse, monkey or other primate, etc.). In some aspects, the subject is a mouse. In some aspects, the subject is a cynomolgus monkey. In some aspects, the subject is a human.

The term "therapeutically effective amount" refers to an amount of a drug, e.g., a humanized anti-SFRP2 antibody or antigen-binding fragment thereof, effective to treat a disease or condition in a subject. In the case of cancer, the therapeutically effective amount of the drug can reduce the number of cancer cells; reduce the tumor size or burden; inhibit (i.e., slow to some extent and in some aspects, stop)

cancer cell infiltration into peripheral organs; inhibit (i.e., slow to some extent and in some aspects, stop) tumor metastasis; inhibit, to some extent, tumor growth; inhibit, to some extent, angiogenesis; relieve to some extent one or more of the symptoms associated with the cancer; and/or result in a favorable response such as increased progression-free survival (PFS), disease-free survival (DFS), or overall survival (OS), complete response (CR), partial response (PR), or, in some cases, stable disease (SD), a decrease in progressive disease (PD), a reduced time to progression (TTP), or any combination thereof. To the extent the drug can prevent growth and/or kill existing cancer cells, it can be cytostatic and/or cytotoxic.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with or suspected of having the disorder. In some aspects, a subject is successfully "treated" for cancer according to the methods provided herein if the patient shows one or more of the following: a reduction in the number of or complete absence of cancer cells: a reduction in tumor size; inhibition of or an absence of cancer cell infiltration into peripheral organs including, for example, the spread of cancer into soft tissue and bone; inhibition of or an absence of tumor metastasis: inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor reduction in the number or frequency of cancer stem cells in a tumor; differentiation of tumorigenic cells to a non-tumorigenic state; increased progression-free survival (PFS), disease-free survival (DFS), or overall survival (OS), complete response (CR), partial response (PR), stable disease (SD), a decrease in progressive disease (PD), a reduced time to progression (TTP), or any combination thereof. In some aspects, treatment comprises: reducing the amount of SFRP2 in a cell by contacting said cell with a humanized anti-SFRP2 antibody or antigen binding fragment thereof as described herein: reducing the serum SFRP2 level of a patient by administering to said patient a therapeutically effective amount of a humanized anti-SFRP2 antibody or antigen binding fragment thereof as described herein; selectively inducing apoptosis of osteosarcoma cells in a patient, e.g., the humanized anti-SFRP2 antibodies do not induce apoptosis in T-cells but do induce apoptosis of osteosarcoma cells; reduction of metastatic osteosarcoma growth in a patient by administering to said patient a therapeutically effective amount of a humanized anti-SFRP2 antibody or antigen binding fragment thereof as described herein; reducing the amount of osteosarcoma lung metastases in a patient by administering to said patient a therapeutically effective amount of a humanized anti-SFRP2 antibody or antigen binding fragment thereof as described herein; reducing the amount of CD38 protein in a patient by administering to said patient a therapeutically effective amount of a humanized anti-SFRP2 antibody or antigen binding fragment thereof as described herein; treating a patient diagnosed with osteosarcoma by administering to said patient a therapeutically effective amount of a humanized anti-SFRP2 antibody or antigen binding fragment thereof as described herein. In some aspects, the treatment is a monotherapy treatment comprising treatment with a humanized anti-SFRP2 antibody or antigen binding fragment thereof as described herein. In some aspects, treatment comprises combination therapy comprising treatment with a humanized anti-SFRP2 antibody or antigen binding fragment thereof as described herein and an antagonist of an inhibitory immune checkpoint molecule, optionally wherein the immune checkpoint molecule is PD-1. In some aspects, the antagonist of PD-1 is an anti-PD-1 antibody or antigen-binding fragment thereof, optionally wherein the anti-PD-1 antibody or antigen-binding fragment thereof is selected from the group consisting of nivolumab, pembrolizumab. MEDI-0680 (AMP-514), camrelizumab (SHR-1210), tislelizumab (BGB-A317), and spartalizumab (NPVPDR001, NVS240118, PDR001).

The terms "cancer" and "cancerous" refer to or describe the physiological condition in mammals in which a population of cells are characterized by unregulated cell growth. In some aspects, a cancer comprises increased expression of SFRP2 and/or SFRP2 expression levels indicative of a diseased state. Examples include, but are not limited to, a breast cancer, a malignant glioma, a multiple myeloma, a renal cell carcinoma, a kidney cancer, a prostate cancer, a lung cancer, a melanoma, a non-small cell lung cancer, a pancreatic cancer, a colorectal cancer, a bladder cancer, a hepatocellular carcinoma, a gastrointestinal cancer, and a sarcoma including, but not limited to an angiosarcoma, an osteosarcoma, a rhabdomyosarcoma, and an alveolar soft part sarcoma.

As used in the present disclosure and claims, the singular forms "a," "an," and "the" include plural forms unless the context clearly dictates otherwise.

It is understood that wherever aspects are described herein with the language "comprising," otherwise analogous aspects described in terms of "consisting of" and/or "consisting essentially of" are also provided. In this disclosure, "comprises," "comprising," "containing" and "having" and the like can mean "includes," "including," and the like; "consisting essentially of" or "consists essentially of" are open-ended, allowing for the presence of more than that which is recited so long as basic or novel characteristics of that which is recited is not changed by the presence of more than that which is recited, but excludes prior art aspects.

Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A. B, and/or C" is intended to encompass each of the following aspects: A, B, and C; A, B, or C; A or C; A or B; B or C; A and C; A and B; B and C; A (alone); B (alone); and C (alone).

As used herein, the terms "about" and "approximately," when used to modify a numeric value or numeric range, indicate that deviations of up to 10% above and down to 10% below the value or range remain within the intended meaning of the recited value or range. It is understood that wherever aspects are described herein with the language "about" or "approximately" a numeric value or range, otherwise analogous aspects referring to the specific numeric value or range are also provided.

"Sequence identity" refers to the extent of identity between two sequences (e.g., amino acid sequences or nucleic acid sequences). Sequence identity can be determined by aligning two sequences, introducing gaps to maximize identity between the sequences. Alignments can be generated using programs known in the art. For purposes herein, alignment of nucleotide sequences can be performed with the blastn program set at default parameters, and alignment of amino acid sequences can be performed with the blastp program set at default parameters (see National Center for Biotechnology Information (NCBI) on the worldwide web, ncbi.nlm.nih.gov).

Any compositions or methods provided herein can be combined with one or more of any of the other compositions and methods provided herein.

6.2 Antibodies

In one aspect, provided herein are humanized antibodies and antigen binding fragments thereof which bind to SFRP2, such as human SFRP2. In a specific aspect, provided herein are humanized antibodies and antigen-binding fragments thereof which specifically bind to human SFRP2. The amino acid sequence of human SFRP2 is known in the at and also provided herein as represented by SEQ ID NO: 12:

MLQGPGSLLLLFLASHCCLGSARGLFLFGQPDFSYKRSNCKPIPVNLQL

CHGIEYQNMRLPNLLGHETMKEVLEQAGAWIPLVMKQCHPDTKKFLCSL

FAPVCLDDLDETIQPCHSLCVQVKDRCAPVMSAFGFPWPDMLECDRFPQ

DNDLCIPLASSDHLLPATEEAPKVCEACKNKNDDDNDIMETLCKNDFAL

KIKVKEITYINRDTKIILETKSKTIYKLNGVSERDLKKSVLWLKDSLQC

TCEEMNDINAPYLVMGQKQGGELVITSVKRWQKGQREFKRISRSIRKLQ

C

In some aspects, a humanized anti-SFRP2 antibody or antigen-binding fragment thereof described herein binds to SFRP2, e.g., human SFRP2, and comprises a VH chain having at least 90% sequence identity, at least 95% sequence identity, at least 99% sequence identity, or 100% sequence identity to a VH chain selected from Table 1:

TABLE 1

| | VH CHAIN AMINO ACID SEQUENCES |
|---|---|
| SEQ ID NO | AMINO ACID SEQUENCE |
| 1 | QVQLVQSGAELKKPGASVKVSCKASGFTFTRYWWHWVRQAPGKGLEWI GRIDPNSGTTRFIEKFKTRATITVDKSTSTAYMHLSSLRSEDSAVYYCARW GPYYGYAMDYWGQGTSVTVSS |
| 2 | QVQLVQSGAELKKPGASVKVSCKASGFTFTRYWWHWVRQAPGKGLEWI GRIDPNSGTTRFIEKFKTRATITVDKSTSTAYMELSSLRSEDSAVYYCARW GPYYGYAMDYWGQGTSVTVSS |
| 3 | QVQLVQSGAEVKKPGASVKVSCKASGFTFTRYWWHWVRQAPGKGLEWI GRIDPNSGTTRFIEKFKTRATITVDKSTSTAYMELSSLRSEDTAVYYCARW GPYYGYAMDYWGQGTLVTVSS |
| 4 | QVQLVQSGAEVKKPGASVKVSCKASGFTFTRYWWHWVRQAPGKGLEWI GRIDPNSGTTRFIEKFKTRVTITVDKSTSTAYMELSSLRSEDTAVYYCARW GPYYGYAMDYWGQGTLVTVSS |

In some aspects, a humanized anti-SFRP2 antibody or antigen-binding fragment thereof described herein binds to SFRP2, e.g., human SFRP2, and comprises a VL chain having at least 90% sequence identity, at least 95% sequence identity, at least 99% sequence identity, or 100% sequence identity to a VL chain selected from Table 2:

TABLE 2

| | VL CHAIN AMINO ACID SEQUENCES |
|---|---|
| SEQ ID NO | AMINO ACID SEQUENCE |
| 5 | QIVLTQSPAILSLSPGERVTITCSASSSVTYMHWYQQKLGKAPKLWIYDTS RLAPGSPARFSGSGSGTDYTLTISSLETEDFASYFCHQWSTYPPTFGQGTKL EIK |
| 6 | QIVLTQSPATLSLSPGERVTITCSASSSVTYMHWYQQKLGKAPKLWIYDTS RLAPGSPARFSGSGSGTDYTLTISSLESEDFASYFCHQWSTYPPTFGQGTKL EIK |
| 7 | QIVLTQSPATLSLSPGERVTITCSASSSVTYMHWYQQKPGKAPKLWIYDTS RLAPGSPARFSGSGSGTDYTLTISSLESEDFASYFCHQWSTYPPTFGQGTKL EIK |
| 8 | QIVLTQSPATLSLSPGERVTITCSASSSVTYMHWYQQKPGKAPKLWIYDTS RLAPGSPARFSGSGSGTDYTLTISSLESEDFATYFCHQWSTYPPTFGQGTKL EIK |
| 9 | QIVLTQSPATLSLSPGERVTITCSASSSVTYMHWYQQKPGKAPKLLIYDTS RLAPGSPARFSGSGSGTDYTLTISSLESEDFATYFCHQWSTYPPTFGQGTKL EIK |

In some aspects, a humanized anti-SFRP2 antibody or antigen-binding fragment thereof described herein binds to SFRP2 e.g., human SFRP2 and comprises a VH chain of Table 1 and a VL chain of Table 2.

In some aspects, a humanized anti-SFRP2 antibody or antigen-binding fragment thereof described herein binds to SFRP2, e.g., human SFRP2, and comprises a VH chain and a VL chain as listed in Table 3.

TABLE 3

| VH/VL Chain Combination | Antibody Identifier |
| --- | --- |
| SEQ ID NO: 1 and SEQ ID NO: 6 | Ab1 |
| SEQ ID NO: 1 and SEQ ID NO: 7 | Ab2 |
| SEQ ID NO: 1 and SEQ ID NO: 8 | Ab3 |
| SEQ ID NO: 1 and SEQ ID NO: 9 | Ab4 |
| SEQ ID NO: 2 and SEQ ID NO: 6 | Ab5 |
| SEQ ID NO: 2 and SEQ ID NO: 7 | Ab6 |
| SEQ ID NO: 2 and SEQ ID NO: 8 | Ab7 |
| SEQ ID NO: 2 and SEQ ID NO: 9 | Ab8 |
| SEQ ID NO: 3 and SEQ ID NO: 6 | Ab9 |
| SEQ ID NO: 3 and SEQ ID NO: 7 | Ab10 |
| SEQ ID NO: 4 and SEQ ID NO: 8 | Ab11 |
| SEQ ID NO: 4 and SEQ ID NO: 9 | Ab12 |
| SEQ ID NO: 3 and SEQ ID NO: 5 | Ab13 |
| SEQ ID NO: 3 and SEQ ID NO: 9 | Ab14 |
| SEQ ID NO: 1 and SEQ ID NO: 5 | Ab15 |
| SEQ ID NO: 2 and SEQ ID NO: 5 | Ab16 |
| SEQ ID NO: 4 and SEQ ID NO: 5 | Ab17 |
| SEQ ID NO: 3 and SEQ ID NO: 8 | Ab18 |
| SEQ ID NO: 4 and SEO ID NO: 6 | Ab19 |
| SEQ ID NO: 4 and SEQ ID NO: 7 | Ab20 |

In some aspects, provided herein are humanized anti-SFRP2 antibodies that comprise a heavy chain and a light chain. With respect to the heavy chain, in some aspects, the heavy chain of a humanized anti-SFRP2 antibody described herein can be an alpha ($\alpha$), delta ($\delta$), epsilon ($\epsilon$), gamma ($\gamma$) or mu ($\mu$) heavy chain. In some aspects, the heavy chain of a humanized anti-SFRP2 antibody described herein can comprise a human alpha ($\alpha$), delta ($\delta$), epsilon ($\epsilon$), gamma ($\gamma$) or mu ($\mu$) heavy chain. In some aspects, a humanized anti-SFRP2 antibody as described herein comprises a heavy chain wherein the amino acid sequence of the VH domain comprises an amino acid sequence set forth in Table 1 and wherein the constant region of the heavy chain comprises the amino acid sequence of a human gamma ($\gamma$) heavy chain constant region. In some aspects, a humanized anti-SFRP2 antibody described herein, e.g., one which binds human SFRP2, comprises a heavy chain wherein the amino acid sequence of the VH domain comprises an amino acid sequence set forth in Table 1 and wherein the constant region of the heavy chain comprises the amino acid sequence of an IgG1 heavy chain constant region. In some aspects, a humanized anti-SFRP2 antibody described herein, e.g., one which binds human SFRP2, comprises a heavy chain wherein the amino acid sequence of the VH domain comprises a sequence set forth in Table 1, and wherein the constant region of the heavy chain comprises the amino acid of a human heavy chain described herein or known in the art. Non-limiting examples of human constant region sequences have been described in the art, e.g., see U.S. Pat. No. 5,693,780 and Kabat E A et al., (1991) supra. In some aspects, the heavy chain comprises a VH domain corresponding to SEQ ID NO: 2. In some aspects, the heavy chain comprises a sequence of SEQ ID NO: 15. In some aspects, the heavy chain is encoded by a polynucleotide sequence of SEQ ID NO:17.

With respect to the light chain, in some aspects, the light chain of a humanized anti-SFRP2 antibody described herein is a kappa light chain. In some aspects, the light chain of a humanized anti-SFRP2 antibody described herein is a lambda light chain. In some aspects, the light chain of a humanized anti-SFRP2 antibody described herein is a human kappa light chain or a human lambda light chain. In some aspects, the light chain of a humanized anti-SFRP2 antibody described herein is a human kappa light chain. In some aspects, the light chain comprises a VL domain corresponding to SEQ ID NO: 9. In some aspects, the light chain comprises a sequence of SEQ ID NO: 16. In some aspects, the light chain is encoded by a polynucleotide sequence of SEQ ID NO:18.

In some aspects, a humanized anti-SFRP2 antibody described herein, e.g., one which binds human SFRP2, comprises a light chain wherein the amino acid sequence of the VL domain comprises a sequence set forth in Table 2, and wherein the constant region of the light chain comprises the amino acid sequence of a human kappa light chain constant region. In some aspects, a humanized anti-SFRP2 antibody described herein, e.g., one which binds human SFRP2, comprises a light chain wherein the amino acid sequence of the VL domain comprises a sequence set forth in Table 2, and wherein the constant region of the light chain comprises the amino acid sequence of a human lambda light chain constant region. In some aspects, a humanized anti-SFRP2 antibody described herein, e.g., one which binds human SFRP2, comprises a light chain wherein the amino acid sequence of the VL domain comprises a sequence set forth in Table 2, and wherein the constant region of the light chain comprises the amino acid sequence of a human kappa or lambda light chain constant region. Non-limiting examples of human constant region sequences have been described in the art, e.g., see U.S. Pat. No. 5,693,780 and Kabat E A et al., (1991) supra.

In some aspects, a humanized anti-SFRP2 antibody described herein, e.g., one which binds human SFRP2, comprises a VH domain and a VL domain comprising the amino acid sequence of any of the humanized anti-SFRP2 antibodies described herein, and wherein the constant regions comprise the amino acid sequences of the constant regions of an IgG, IgE, IgM, IgD, IgA, or IgY immunoglobulin molecule, or a human IgG, IgE, IgM, IgD, IgA, or IgY immunoglobulin molecule. In some aspects, a humanized anti-SFRP2 antibody described herein, e.g., one which binds human SFRP2, comprises a VH domain and a VL domain comprising the amino acid sequences of any of the humanized anti-SFRP2 antibodies described herein, and wherein the constant regions comprise the amino acid sequences of the constant regions of an IgG, IgE, IgM, IgD, IgA, or IgY immunoglobulin molecule, any class (e.g., IgG1, IgG2, IgG3, IgG4, IgA1, and IgA2), or any subclass (e.g., IgG2a and IgG2b) of immunoglobulin molecule. In some aspects, the constant regions comprise the amino acid sequences of the constant regions of a human IgG, IgE, IgM, IgD, IgA, or IgY immunoglobulin molecule, any class (e.g., IgG1, IgG2, IgG3, IgG4, IgA1, and IgA2), or any subclass (e.g., IgG2a and IgG2b) of immunoglobulin molecule.

In some aspects, a humanized anti-SFRP2 antibody described herein, e.g., one which binds human SFRP2, comprises a heavy chain wherein the amino acid sequence of the VH domain comprises an amino acid sequence set forth in Table 1 and wherein the constant region of the heavy chain comprises the amino acid sequence of an IgG1 heavy chain constant region: and/or comprises a light chain wherein the amino acid sequence of the VL domain comprises a sequence set forth in Table 2, and wherein the constant region of the light chain comprises the amino acid sequence of a human kappa light chain constant region.

In some aspects, a humanized anti-SFRP2 antibody or antigen-binding fragment thereof described herein, e.g., one which binds human SFRP2, comprises a heavy chain and a light chain, wherein (i) the heavy chain comprises a VH domain comprising the amino acid sequence of an antibody listed in Table 1 (e.g., SEQ ID NO: 1, 2, 3, or 4); (ii) the light chain comprises a VL domain comprising the amino acid sequence of the same antibody listed in Table 2 (e.g., SEQ ID NO: 5, 6, 7, 8, or 9): (iii) the heavy chain further comprises a constant heavy chain domain comprising the amino acid sequence of the constant domain of a human IgG1 heavy chain; and (iv) the light chain further comprises a constant light chain domain comprising the amino acid sequence of the constant domain of a human kappa light chain. In some aspects, a humanized anti-SFRP2 antibody described herein or antigen-binding fragment thereof, e.g., one which binds human SFRP2, comprises a heavy chain and a light chain, wherein the heavy chain comprises an amino acid sequence of SEQ ID NO: 15 and/or wherein the light chain comprises an amino acid sequence of SEQ ID NO: 16. In some aspects, the heavy chain comprises an amino acid sequence with at least 90% sequence identity, at least 95% sequence identity, at least 99% sequence identity, or 100% sequence identity to SEQ ID NO: 15. In some aspects, the light chain comprises an amino acid sequence with at least 90% sequence identity, at least 95% sequence identity, at least 99% sequence identity, or 100% sequence identity to SEQ ID NO: 16. In some aspects, the heavy chain and/or light chain comprises an amino acid sequence set forth in Table 4.

sequence of SEQ ID NO:22, a CDR L2 comprising the amino acid sequence of SEQ ID NO:23, and a CDR L3 comprising the amino acid sequence of SEQ ID NO:24. In some aspects, the humanized anti-SFRP2 antibody comprises the CDR sequences comprising the amino acid sequences set forth in Table 5.

TABLE 5

COMPLEMENTARY DETERMINING REGION AMINO ACID SEQUENCES

| SEQ ID NO | AMINO ACID SEQUENCE |
|---|---|
| 19 (CDR H1) | RYWWH |
| 20 (CDR H2) | RIDPNSGTTRFIEKFKT |
| 21 (CDR H3) | WGPYYGYAMDY |
| 22 (CDR L1) | SASSSVTYMH |
| 23 (CDR L2) | DTSRLAP |
| 24 (CDR L3) | HQWSTYPPT |

Non-limiting examples of human constant regions are described in the art, e.g., see Kabat E A et al., (1991) supra.

In some aspects, an anti-SFRP2 antibody or antigen binding fragment thereof comprises a chimeric antibody. In

TABLE 4

HEAVY CHAIN AND LIGHT CHAIN AMINO ACID SEQUENCES

| SEQ ID NO | AMINO ACID SEQUENCE |
|---|---|
| 15 (Heavy Chain) | QVQLVQSGAELKKPGASVKVSCKASGFTFTRYWWHWVRQAPGKGLE WIGRIDPNSGTTRFIEKFKTRATITVDKSTSTAYMELSSLRSEDSAVYYCA RWGPYYGYAMDYWGQGTSVTVSSASTKGPSVFPLAPSSKSTSGGTAAL GCLVKDYFPEPVTVSWNSGALTSGVHTFPAVLQSSGLYSLSSVVTVPSSS LGTQTYICNVNHKPSNTKVDKKVEPKSCDKTHTCPPCPAPELLGGPSVFL FPPKPKDTLMISRTPEVTCVVVDVSHEDPEVKFNWYVDGVEVHNAKTK PREEQYNSTYRVVSVLIVLHQDWLNGKEYKCKVSNKALPAPIEKTISKA KGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHY TQKSLSLSPGK |
| 16 (Light Chain) | QIVLTQSPATLSLSPGERVTITCSASSSVTYMHWYQQKPGKAPKLLIYDT SRLAPGSPARFSGSGSGTDYTLTISSLESEDFATYFCHQWSTYPPTFGQGT KLEIKRTVAAPSVFIFPPSDEQLKSGTASVVCLLNNFYPREAKVQWKVD NALQSGNSQESVTEQDSKDSTYSLSSTLTLSKADYEKHKVYACEVTHQG LSSPVTKSFNRGEC |

In some aspects, a humanized anti-SFRP2 antibody described herein, e.g., one which binds human SFRP2, comprises a heavy chain and a light chain, wherein the heavy chain comprises a VH domain comprising an amino acid sequence of SEQ ID NO: 2 and/or wherein the light chain comprises a VL domain comprising an amino acid sequence of SEQ ID NO: 9.

In some aspects, a humanized anti-SFRP2 antibody described herein, e.g., one which binds human SFRP2, comprises a complementary determining region (CDR) H1 comprising the amino acid sequence of SEQ ID NO:19, a CDR H2 comprising the amino acid sequence of SEQ ID NO:20, a CDR H3 comprising the amino acid sequence of SEQ ID NO:21, a CDR L1 comprising the amino acid some aspects, a chimeric anti-SFRP2 antibody comprises a VH chain polypeptide of SEQ ID NO: 10 and a VL chain polypeptide of SEQ ID NO: 11 (referred to as Chi.1). In some aspects, a chimeric anti-SFRP2 antibody comprises a VH chain polypeptide of SEQ ID NO: 10 and a VL chain polypeptide of SEQ ID NO: 13 (referred to as Chi.2). In some aspects, a chimeric anti-SFRP2 antibody comprises human constant regions, such as any of those discussed herein. In some instances, a chimeric anti-SFRP2 antibody comprises an IgG1 constant region.

6.3 Antibody Activities

In some aspects, a humanized anti-SFRP2 antibody described herein, e.g., one that binds human SFRP2, comprises an IC50 value of 0.7 or less, 0.6 or less, or 0.5 or less relative to the IC50 value of an antibody or antigen binding fragment thereof comprising a VH chain polypeptide and VL chain polypeptide of SEQ ID NOs: 10 and 11, respectively. Relative IC50 values can be calculated, for example, using the methods described in Example 2. For instance, humanized anti-SFRP2 antibodies or antigen binding fragments thereof can be prepared as a dilution series and subsequently be premixed with a constant concentration of biotinylated antibody comprising SEQ ID NOs: 10 and 11 prior to incubation at room temperature on a microtitre plate pre-coated with Peptide B (SEQ ID NO: 14), which peptide comprises amino acids 202-220 of human SFRP2 (SEQ ID NO: 12). The results obtained from the competitive ELISA analysis can be used to calculate $IC_{50}$ values for each antibody, which values can then be normalized to the $IC_{50}$ value of the antibody comprising SEQ ID NOs: 10 and 11 that was included on each ELISA plate.

In some aspects, a humanized anti-SFRP2 antibody described herein, e.g., one that binds human SFRP2, inhibits endothelial tube formation. Inhibition of endothelial tube formation can be measured as described in Example 2. For instance, an endothelial tube formation assay using 2H11 cells can be performed, in which 2H11 mouse endothelial cells treated with SFRP2, which promotes tube formation, are further treated with humanized anti-SFRP2 antibodies or control antibodies, e.g., IgG1 treatment, and the number of branch points measured and compared to positive and negative controls. Also, an endothelial tube formation assay using SVR angiosarcoma cells can be performed, in which SVR angiosarcoma cells are treated with humanized anti-SFRP2 antibodies or control antibodies, e.g., IgG1 treatment, and the number of branch points counted and/or the percent of inhibition calculated. As demonstrated by the results of such a tube formation assay, the humanized anti-SFRP2 antibody Ab8 was the only antibody to statistically significantly inhibit tube formation versus the control treatment (*p=0.03). This result was surprising as, for example, the heavy chain of Ab8 differs from the heavy chain of Ab2 and Ab3 by a single amino acid, while the light chain of Ab8 differs from the light chain of Ab11 in a single amino acid. However, Ab2, Ab3, and Ab11 did not statistically significantly inhibit tube formation. As such, the results of such an endothelial tube formation assay demonstrate the unique and surprising properties of a humanized anti-SFRP2 antibody comprising the variable heavy chain amino acid sequence of SEQ ID NO: 2 and the variable light chain amino acid sequence of SEQ ID NO: 9. i.e., Ab8.

In some aspects, a humanized anti-SFRP2 antibody described herein, e.g., one that binds human SFRP2, induces apoptosis of SFRP2-expressing osteosarcoma cells. In some aspects, such induction of apoptosis can be measured as described in Example 3. For instance, RF577 cell line, which expresses SFRP2 endogenously, can be plated and subsequently treated varying concentrations of humanized anti-SFRP2 antibody or IgG1 control antibody and apoptosis measured using techniques known in the art. In some aspects, apoptosis of osteosarcoma cells is increased by 10% or more, 20% or more, 30% or more, or 40% or more as compared to a control treatment, e.g., treatment with IgG antibody. In some aspects, humanized anti-SFRP2 antibody-induced induction of apoptosis of SFRP2-expressing osteosarcoma cells is selective, e.g., the humanized anti-SFRP2 antibodies do not induce apoptosis in T-cells. In some instances, such a measurement can be performed as described in Example 3. For instance, CD4+ and CD8+ cells can be isolated from a source, e.g., mouse splenocytes, according to methods known in the art and subsequently treated with a humanized anti-SFRP2 antibody or control, e.g., IgG1, antibody. Following treatment, cells can be stained and analyzed by flow cytometry to detect the measure apoptosis of the cells. In some aspects, the percentage of apoptotic cells is unchanged as compared to a control sample, and/or the percentage of apoptotic cells is less than the number of cells in a positive control in which apoptosis occurs.

In some aspects, a humanized anti-SFRP2 antibody described herein, e.g., one which binds human SFRP2, inhibits osteosarcoma-related lung metastases as either a monotherapy or when administered in combination with a PD-1 inhibitor, e.g., a PD-1 mAb. Such inhibition can be measured as generally described in Example 6. For instance, osteosarcoma lung metastases can be generated by tail vein injection in C57/Bl6 mice with RF577 tumor cells. Treatments can be started after a pre-determined length of time, e.g., 12 days, following tumor cell injection, which treatments include IgG1 control antibody, humanized anti-SFRP2 antibody, PD-1 inhibitor, or a combination of humanized anti-SFRP2 antibody and PD-1 inhibitor. After a predetermined length of time, the lungs of the mice can be analyzed using high-resolution photographs were taken and the number metastatic surface lung nodules quantitated for each treatment group. In some aspects, treatment with a humanized anti-SFRP2 antibody or antigen binding fragment thereof reduces the number of lung surface metastasis compared to the IgG1 control, either when administered as a monotherapy or in combination with an antagonist of an inhibitory immune checkpoint molecule, optionally wherein the immune checkpoint molecule is PD-1. In some aspects, an SFRP2 antibody or antigen binding fragment thereof reduces lung metastatic tumor volume compared to a control by 50% or more, 60% or more, 70% or more, or 80% or more, e.g., when administered as a monotherapy, e.g., when administered in combination with an antagonist of an inhibitory immune checkpoint molecule.

In some aspects, a humanized anti-SFRP2 antibody described herein, e.g., one that binds human SFRP2, reduces SFRP2 serum levels as either a monotherapy or when administered in combination with an antagonist of an inhibitory immune checkpoint molecule, optionally wherein the immune checkpoint molecule is PD-1. Such reduction can be measured as generally described in Example 4. For instance, blood from control mice or RF577-bearing mice treated with IgG1 control antibody, humanized anti-SFRP2 antibody, antagonist of an inhibitory immune checkpoint molecule, e.g., PD-1 inhibitor, or a combination of both antibodies can be collected and separation of serum performed. The serum samples can then be processed using the RayBiotech Mouse SFRP2 ELISA kit (ELM-SFRP-2; Peachtree Corners, GA, USA) following the manufacturer protocol. In some aspects humanized anti-SFRP2 antibody described herein, e.g., one which binds human SFRP2, reduces SFRP2 serum levels either a monotherapy or when administered in combination with an antagonist of an inhibitory immune checkpoint molecule as compared to a control, e.g., treatment with IgG1.

In some aspects, a humanized anti-SFRP2 antibody described herein, e.g., one that binds human SFRP2, reduces CD38 levels. Such reduction can be measured as generally described in Example 5. For instance, mice with RF577 OS lung metastases can be prepared known in the art, and splenocytes harvested from these mice at a predetermined time. After harvesting, the splenocytes can be treated with IgG1 control antibody or a humanized anti-SFRP2 antibody.

Following treatment, the splenocytes can be lysed and prepared for Western blot analysis probing for CD38 levels using standard protocols. In some aspects, a humanized anti-SFRP2 antibody described herein reduces CD38 levels by 50% or more, 60% or more, 70% or more, or 80% or more as compared to a control, e.g., treatment with IgG1.

6.4 Antigen Binding Fragments

In some aspects, an antigen-binding fragment of a humanized anti-SFPR2 antibody described herein, e.g., a humanized anti-SFRP2 antibody that binds human SFRP2, is provided. Exemplary antigen-binding fragments include but are not limited to Fab, Fab', F(ab')2, and scFv, wherein the Fab, Fab', F(ab')2, or scFv comprises a heavy chain variable region sequence and a light chain variable region sequence of a humanized anti-SFRP2 antibody as described herein. A Fab, Fab', F(ab')2, or scFv can be produced by any technique known to those of skill in the art, including, but not limited to, those discussed infra. In some aspects, an antigen-binding fragment, such as a Fab, Fab', F(ab')2, or scFv, further comprises a moiety that extends the half-life of the antibody in vivo. The moiety is also termed a "half-life extending moiety." Any moiety known to those of skill in the art for extending the half-life of an antigen-binding fragment, such as a Fab, Fab', F(ab')2, or scFv, in vivo can be used. For example, the half-life extending moiety can include an Fc region, a polymer, an albumin. or an albumin binding protein or compound. The polymer can include a natural or synthetic, optionally substituted straight or branched chain polyalkylene, polyalkenylene, polyoxylalkylene, polysaccharide, polyethylene glycol, polypropylene glycol, polyvinyl alcohol, methoxypolyethylene glycol, lactose, amylose, dextran, glycogen, or derivative thereof. Substituents can include one or more hydroxy, methyl, or methoxy groups. In some aspects, an antigen-binding fragment, such as an Fab, Fab', F(ab')2, or scFv, can be modified by the addition of one or more C-terminal amino acids for attachment of the half-life extending moiety. In some aspects, the half-life extending moiety is polyethylene glycol or human serum albumin. In some aspects, an antigen-binding fragment, such as a Fab, Fab', F(ab')2, or scFv, is fused to a Fc region.

A humanized anti-SFRP2 antibody or antigen-binding fragment thereof can be fused or conjugated (e.g., covalently or noncovalently linked) to a detectable label or substance. Examples of detectable labels or substances include enzyme labels, such as, glucose oxidase; radioisotopes, such as iodine (125I, 121I), carbon (14C), sulfur (35S), tritium (3H), indium (121In), and technetium (99Tc); luminescent labels, such as luminol; and fluorescent labels, such as fluorescein and rhodamine, and biotin.

6.5 Antibody Production

Humanized anti-SFRP2 antibodies and antigen binding fragments thereof can be produced by any method known in the art for the synthesis of humanized antibodies and antigen-binding fragments. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Sambrook J et al., (2001) Molecular Cloning: A Laboratory Manual, Cold Spring Harbor Laboratory Press, Cold Spring Harbor, NY; Ausubel F M et al., Current Protocols in Molecular Biology, John Wiley & Sons (1987 and annual updates); Current Protocols in Immunology, John Wiley & Sons (1987 and annual updates); Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a certain aspect, provided herein is a method of making a humanized anti-SFRP2 antibody or antigen binding fragment thereof comprising culturing a cell or host cell described herein (e.g., a cell or a host cell comprising polynucleotides encoding an antibody or antigen-binding fragment thereof described herein). In a certain aspect, provided herein is a method of making a humanized anti-SFRP2 antibody or antigen binding fragment thereof comprising expressing (e.g., recombinantly expressing) the antibody or antigen-binding fragment thereof using a cell or host cell described herein (e.g., a cell or a host cell comprising polynucleotides encoding an antibody or antigen-binding fragment thereof described herein). In some aspects, the cell is an isolated cell. In some aspects, the encoding polynucleotides have been introduced into the cell. In some aspects, the method further comprises the step of purifying the antibody or antigen-binding fragment obtained from the cell or host cell.

Monoclonal antibodies or antigen-binding fragments thereof can be prepared using a wide variety of techniques known in the art including the use of hybridoma, recombinant, and phage display technologies, yeast-based presentation technologies, or a combination thereof. For example, monoclonal antibodies or antigen-binding fragments thereof can be produced using hybridoma techniques including those known in the art and taught, for example, in Harlow E & Lane D. Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), or as described in Kohler G & Milstein C (1975) Nature 256: 495. Examples of yeast-based presentation methods that can be employed to select and generate the antibodies described herein include those disclosed in, for example, WO2009/036379A2; WO20101105256; and WO2012/009568, each of which is herein incorporated by reference in its entirety.

In some aspects, a monoclonal antibody or antigen-binding fragment is an antibody or antigen-binding fragment produced by a clonal cell (e.g., hybridoma or host cell producing a recombinant antibody or antigen-binding fragment), wherein the antibody or antigen-binding comprises a humanized anti-SFRP2 antibody or antigen binding fragment thereof. In some aspects, a monoclonal antibody or antigen-binding fragment thereof can be a Fab fragment or a F(ab')2 fragment. Monoclonal antibodies or antigen-binding fragments thereof described herein can, for example, be made by the hybridoma method as described in Kohler G & Milstein C (1975) Nature 256: 495, or can, e.g., be isolated from phage libraries using the techniques as described herein, for example. Other methods for the preparation of clonal cell lines and of monoclonal antibodies and antigen-binding fragments thereof expressed thereby are well known in the art (see, for example. Chapter 11 in: Short Protocols in Molecular Biology, (2002) 5th Ed., Ausubel F M et al., supra).

Antigen-binding fragments of antibodies described herein can be generated by any technique known to those of skill in the art. For example, Fab and F(ab')2 fragments described herein can be produced by proteolytic cleavage of immunoglobulin molecules, using enzymes such as papain (to produce Fab fragments) or pepsin (to produce F(ab')2 fragments). A Fab fragment corresponds to one of the two identical arms of a tetrameric antibody molecule and contains the complete light chain paired with the VH and CH1 domains of the heavy chain. A F(ab')2 fragment contains the two antigen-binding arms of a tetrameric antibody molecule linked by disulfide bonds in the hinge region.

In some aspects, a humanized anti-SFRP2 antibody or antigen binding fragment thereof as described herein is produced by culturing a host cell, such as a CHO cell, such that a nucleic acid molecule(s) encoding the antibody or antigen-binding fragment thereof is expressed, thereby producing the humanized anti-SFRP2 antibody or antigen binding fragment thereof, and optionally isolating the antibody or antigen-binding fragment thereof from the culture. In some aspects, the host cell is a CHO cell. In some aspects, the isolated antibody or antigen-binding fragment thereof is substantially free of precipitates, i.e., free of precipitates when inspected by, for example, eye, A280, size exclusion chromatography, and/or dynamic light scattering. In some aspects, a humanized anti-SFRP2 antibody or antigen binding fragment thereof as described herein is produced by CHO cells transduced with a vector, e.g., vector collected from 293 GP cells transfected with retrovector (GPEX vector) made from the gene construct developed to express the humanized antibody or antigen binding fragment described herein.

6.6 Polynucleotides

In certain aspects, provided herein are polynucleotides comprising a nucleotide sequence encoding a humanized anti-SFRP2 antibody or antigen binding fragment thereof, and vectors, e.g., vectors comprising such polynucleotides for recombinant expression in host cells (e.g., E. coli and mammalian cells).

In particular aspects, provided herein are polynucleotides comprising nucleotide sequences encoding humanized anti-SFRP2 antibodies or antigen binding fragment thereof described herein and comprise an amino acid sequences as described herein.

Also provided herein is a polynucleotide comprising a nucleotide sequence encoding a polypeptide comprising a sequence selected from the group consisting of SEQ ID NOs: 1-9 and SEQ ID NOs: 15-16.

Also provided herein are kits, vectors, or host cells comprising (i) a first polynucleotide comprising a nucleotide sequence encoding an amino acid sequence of SEQ ID NO: 1, 2, 3, or 4; and (ii) a second polynucleotide comprising a nucleotide sequence encoding an amino acid sequence of SEQ ID NO: 5, 6, 7, 8, or 9. In a kit comprising such first and second polynucleotides, the first and second polynucleotides can be in the same vector or can be in different vectors. In a host cell comprising such first and second polynucleotides, the first and second polynucleotides can in the same vector or can be in different vectors.

In some aspects, provided herein are polynucleotides comprising a nucleotide sequence encoding a humanized anti-SFRP2 antibody or an antigen binding fragment thereof or a fragment thereof comprising a VH domain comprising an amino acid sequence described herein (e.g., see Table 1). In some aspects, provided herein are polynucleotides comprising a nucleotide sequence encoding a humanized anti-SFRP2 antibody or an antigen binding fragment thereof comprising a VL domain comprising an amino acid sequence described herein (e.g., see Table 2).

In some aspects, a polynucleotide comprises a nucleic acid sequence encoding a heavy chain variable region (e.g., a VH comprising the amino acid sequence of SEQ ID NO: 1, 2, 3, or 4) and a heavy chain constant region, e.g., a human gamma (γ) heavy chain constant region, e.g., human IgG1 constant region.

In some aspects, a polynucleotide comprises a nucleic acid sequence encoding a light chain variable region (e.g., a VL comprising the amino acid sequence of SEQ ID NO: 5, 6, 7, 8, or 9) and a light chain constant region, e.g., a human lambda or kappa light chain constant region, e.g., a human kappa light chain constant region.

Also provided herein are polynucleotides encoding a humanized anti-SFRP2 antibody or antigen binding fragment thereof described herein or a domain thereof that are optimized, e.g., by codon/RNA optimization, replacement with heterologous signal sequences, and elimination of mRNA instability elements. Methods to generate optimized nucleic acids encoding a humanized anti-SFRP2 antibody or antigen-binding fragment thereof or a domain thereof (e.g., heavy chain, light chain, VH domain, or VL domain) for recombinant expression by introducing codon changes (e.g., a codon change that encodes the same amino acid due to the degeneracy of the genetic code, see Table 6 herein below) and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly.

A polynucleotide encoding an antibody or antigen-binding fragment thereof described herein or a domain thereof can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody or antigen-binding fragment thereof. Such PCR amplification methods can be used to obtain nucleic acids comprising the sequence encoding the variable light chain region and/or the variable heavy chain region of an antibody or antigen-binding fragment thereof. The amplified nucleic acids can be cloned into vectors for expression in host cells and for further cloning, for example, to generate humanized antibodies or antigen-binding fragments thereof.

Polynucleotides provided herein can be, e.g., in the form of RNA or in the form of DNA. DNA includes cDNA, genomic DNA, and synthetic DNA, and DNA can be double-stranded or single-stranded. If single stranded, DNA can be the coding strand or non-coding (anti-sense) strand. In some aspects, the polynucleotide is a cDNA or a DNA lacking one more endogenous introns. In some aspects, a polynucleotide is a non-naturally occurring polynucleotide. In some aspects, a polynucleotide is recombinantly produced. In some aspects, the polynucleotides are isolated. In some aspects, the polynucleotides are substantially pure. In some aspects, a polynucleotide is purified from natural components.

6.7 Cells and Vectors

In certain aspects, provided herein are vectors (e.g., expression vectors) comprising polynucleotides comprising nucleotide sequences encoding humanized anti-SFRP2 antibodies and antigen-binding fragments thereof or a domain thereof for recombinant expression in host cells, preferably in mammalian cells. Also provided herein are cells, e.g. host cells, comprising such vectors for recombinantly expressing humanized anti-SFRP2 antibodies or antigen-binding fragments thereof described herein, e.g., Ab1-Ab20, e.g., an antibody comprising a VH chain polypeptide of SEQ ID NO: 1, 2, 3, or 4; and comprising a VL chain polypeptide of SEQ ID NO: 5, 6, 7, 8, or 9. In some aspects, provided herein are methods for producing an antibody or antigen-binding fragments thereof described herein, comprising expressing such antibody or antigen-binding fragment thereof in a host cell.

In some aspects, recombinant expression of a humanized anti-SFRP2 antibody or antigen-binding fragment thereof or domain thereof described herein (e.g., a heavy or light chain described herein) involves construction of an expression vector containing a polynucleotide that encodes the antibody or antigen-binding fragment thereof or domain thereof. Once a polynucleotide encoding an antibody or antigen-binding fragment thereof or domain thereof (e.g., heavy or light chain variable domain) described herein has been obtained, the vector for the production of the antibody or antigen-binding fragment thereof can be produced by recombinant DNA technology using techniques well known in the art. Thus, methods for preparing a protein by expressing a polynucleotide containing an antibody or antigen-binding fragment thereof or domain thereof (e.g., light chain or heavy chain) encoding nucleotide sequence are described herein. Methods which are well known to those skilled in the art can be used to construct expression vectors containing antibody or antigen-binding fragment thereof or domain thereof (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody or antigen-binding fragment thereof described herein, a heavy or light chain, a heavy or light chain variable domain, or a heavy or light chain CDR, operably linked to a promoter. Such vectors can, for example, include the nucleotide sequence encoding the constant region of the antibody or antigen-binding fragment thereof (see, e.g., International Publication Nos. WO 86/05807 and WO 89/01036; and U.S. Pat. No. 5,122,464), and variable domains of the antibody or antigen-binding fragment thereof can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody or antigen-binding fragment thereof described herein, e.g., Ab1-Ab20, e.g., an antibody comprising a VH chain polypeptide of SEQ ID NO: 1, 2, 3, or 4; and comprising a VL chain polypeptide of SEQ ID NO: 5, 6, 7, 8, or 9. Thus, provided herein are host cells containing a polynucleotide encoding an antibody or antigen-binding fragment thereof described herein, e.g., Ab1-Ab20, e.g., an antibody comprising a VH chain polypeptide of SEQ ID NO: 1, 2, 3, or 4; and comprising a VL chain polypeptide of SEQ ID NO: 5, 6, 7, 8, or 9, or a domain thereof, operably linked to a promoter for expression of such sequences in the host cell. In some aspects, for the expression of double-chained antibodies or antigen-binding fragments thereof, vectors encoding both the heavy and light chains, individually, can be co-expressed in the host cell for expression of the entire immunoglobulin, as detailed below. In some aspects, a host cell contains a vector comprising a polynucleotide encoding both the heavy chain and light chain of an antibody described herein, e.g., Ab1-Ab20, e.g., an antibody comprising a VH chain polypeptide of SEQ ID NO: 1, 2, 3, or 4; and comprising a VL chain polypeptide of SEQ ID NO: 5, 6, 7, 8, or 9, or a domain thereof. In some aspects, a host cell contains two different vectors, a first vector comprising a polynucleotide encoding a heavy chain or a heavy chain variable region of an antibody or antigen-binding fragment thereof described herein, and a second vector comprising a polynucleotide encoding a light chain or a light chain variable region of an antibody described herein, or a domain thereof. In some aspects, a first host cell comprises a first vector comprising a polynucleotide encoding a heavy chain or a heavy chain variable region of an antibody or antigen-binding fragment thereof described herein, and a second host cell comprises a second vector comprising a polynucleotide encoding a light chain or a light chain variable region of an antibody or antigen-binding fragment thereof described herein (e.g., an antibody or antigen-binding fragment thereof. In some aspects, a heavy chain/heavy chain variable region expressed by a first cell associated with a light chain/light chain variable region of a second cell to form a humanized anti-SFRP2 antibody or antigen-binding fragment thereof described herein. In some aspects, provided herein is a population of host cells comprising such first host cell and such second host cell.

In some aspects, provided herein is a population of vectors comprising a first vector comprising a polynucleotide encoding a light chain-light chain variable region of a humanized anti-SFRP2 antibody or antigen-binding fragment thereof described herein, and a second vector comprising a polynucleotide encoding a heavy chain/heavy chain variable region of a humanized anti-SFRP2 antibody or antigen-binding fragment thereof described herein. Alternatively, a single vector can be used which encodes, and is capable of expressing, both heavy and light chain polypeptides.

A variety of host-expression vector systems can be utilized to express antibodies and antigen-binding fragments thereof described herein (e.g., an antibody or antigen-binding fragment thereof comprising a VH chain polypeptide of SEQ ID NO: 1, 2, 3, or 4; and comprising a VL chain polypeptide of SEQ ID NO: 5, 6, 7, 8, or 9)(see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody or antigen-binding fragment thereof described herein in situ. These include but are not limited to microorganisms such as bacteria (e.g., *E. coli* and *B. subtils*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences: or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In some aspects, cells for expressing antibodies and antigen-binding fragments thereof described herein (e.g., an antibody or antigen-binding fragment thereof comprising a VH chain polypeptide of SEQ ID NO: 1, 2, 3, or 4; and comprising a VL chain polypeptide of SEQ ID NO: 5, 6, 7, 8, or 9) are CHO cells, for example GPEx® Chinese Hamster Ovary (GCHO) cell line. In some aspects, cells for expressing antibodies described herein are human cells, e.g., human cell lines. In some aspects, a mammalian expression vector is pOptiVEC™ or pcDNA3.3. In some aspects, bacterial cells such as E. coli, or eukaryotic cells (e.g., mammalian cells), especially for the expression of whole recombinant antibody molecule, are used for the expression of a recombinant antibody molecule. For example, mammalian cells such as Chinese hamster ovary (CHO) cells in conjunction with a vector such as the major intermediate early gene promoter element from human cytomegalovirus is an effective expression system for antibodies (Foecking M K & Hofstetter H (1986) Gene 45: 101-105; and Cockett M I et al., (1990) Biotechnology 8: 662-667). In some aspects, antibodies or antigen-binding fragments thereof described herein are produced by CHO cells or NS0 cells. In some aspects, antibodies or antigen-binding fragments thereof described herein are produced by CHO cells transduced with a vector.

In addition, a host cell strain can be chosen which modulates the expression of the inserted sequences, or modifies and processes the gene product in the specific fashion desired. Such modifications (e.g., glycosylation) and processing (e.g., cleavage) of protein products can contribute to the function of the protein. To this end, eukaryotic host cells that possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immuoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In some aspects, humanized anti-SFRP2 antibodies or antigen-binding fragments thereof described herein (an antibody or antigen-binding fragment thereof comprising a VH chain polypeptide of SEQ ID NO: 1, 2, 3, or 4; and comprising a VL chain polypeptide of SEQ ID NO: 5, 6, 7, 8, or 9) are produced in mammalian cells, such as CHO cells.

Once an antibody or antigen-binding fragment thereof described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies or antigen-binding fragments thereof described herein can be fused to heterologous polypeptide sequences described herein or otherwise known in the art to facilitate purification.

In some aspects, an antibody or antigen-binding fragment thereof described herein is isolated or purified. Generally, an isolated antibody or antigen-binding fragment thereof is one that is substantially free of other antibodies or antigen-binding fragments thereof with different antigenic specificities than the isolated antibody or antigen-binding fragment thereof. For example, in some aspects, a preparation of an antibody or antigen-binding fragment thereof described herein is substantially free of cellular material and/or chemical precursors. Moreover, in some aspects, an antibody or antigen-binding fragment thereof described herein is isolated or purified, e.g., partially purified, and the isolated or purified antibody or antigen binding fragment thereof is substantially free of precipitates, i.e., free of precipitates when inspected by, for example, eye, A280, size exclusion chromatography, and/or dynamic light scattering.

6.8 Pharmaceutical Compositions

Provided herein are compositions comprising a humanized anti-SFRP2 antibody or antigen-binding fragment thereof as described herein, and, in some instances, further comprising an antagonist of an inhibitory immune checkpoint molecule. In some aspects, the humanized anti-SFRP2 antibody or antigen binding fragment thereof having the desired degree of purity is present in a pharmaceutical composition comprising, e.g., a physiologically acceptable carrier, excipient or stabilizer (Remington's Pharmaceutical Sciences (1990) Mack Publishing Co., Easton. PA). Acceptable carriers, excipients, or stabilizers are nontoxic to recipients at the dosages and concentrations employed. Formulations suitable for parenteral administration include aqueous and non-aqueous, isotonic sterile injection solutions, which can comprise antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

In some aspects, the pharmaceutical composition comprises phosphate buffered saline (PBS), e.g., PBS at about pH 7.4. In some aspects, the pharmaceutical formulation comprises sodium acetate and/or sodium chloride, e.g., about 10 mM sodium acetate and about 100 mM sodium chloride at a pH of about 5.5. In some aspects, the pharmaceutical formulation comprises sodium acetate and/or sodium chloride, e.g., about 20 mM sodium acetate and about 100 mM sodium chloride at a pH of about 5.5. In some aspects, the pharmaceutical formulation comprises citrate and/or sodium chloride, e.g., about 10 mM citrate and about 150 mM sodium chloride at a pH of about 5. In some aspects, the pharmaceutical formulation comprises citrate and/or sodium chloride, e.g., about 20 mM citrate and about 150 mM sodium chloride at a pH of about 5. In some aspects, the pharmaceutical formulation comprises histidine and/or sodium chloride, e.g., about 10 mM citrate and about 150 mM sodium chloride at a pH of about 6. In some aspects, the pharmaceutical formulation comprises histidine and/or sodium chloride, e.g., about 20 mM citrate and about 150 mM sodium chloride at a pH of about 6. In some aspects, the pharmaceutical formulation comprises phosphate and/or sodium chloride, e.g., about 10 mM phosphate and about 150 mM sodium chloride at a pH of about 7. In some aspects, the pharmaceutical formulation comprises phosphate and/or sodium chloride, e.g., about 20 mM phosphate and about 150 mM sodium chloride at a pH of about 7. In some aspects, the pharmaceutical formulation comprises phosphate and/or sodium chloride, e.g., about 10 mM phosphate and about 150 mM sodium chloride at a pH of about 8. In some aspects, the pharmaceutical formulation comprises phosphate and/or sodium chloride, e.g., about 20 mM phosphate and about 150 mM sodium chloride at a pH of about 8. In some aspects, the pharmaceutical formulation comprises tis and/or sodium chloride, e.g., about 10 mM phosphate and about 150 mM sodium chloride at a pH of about 9. In some aspects, the pharmaceutical formulation comprises tris and/or sodium chloride, e.g., about 20 mM phosphate and about 150 mM sodium chloride at a pH of about 9. In some aspects, the pharmaceutical composition comprises one or more excipients. In some aspects, the one or more excipients comprise sodium chloride, a polysorbate, e.g., polysorbate 80, sucrose, and/or arginine. In some aspects, the pharmaceutical composition comprises a buffer at a desired pH, and further comprises sodium chloride, e.g., about 100 mM sodium chloride, e.g., about 120 mM sodium chloride. In some aspects, the pharmaceutical composition comprises a buffer at a desired pH, and further comprises sodium chloride and a polysorbate, e.g., about 120 mM sodium chloride and 0.01% polysorbate 80; e.g., 150 mM NaCl and 0.05% polysorbate 20, e.g., 75 mM NaCl and 0.05% polysorbate 20. In some aspects, the pharmaceutical composition comprises a buffer at a desired pH, and further comprises sucrose, e.g., about 6% sucrose. In some aspects, the pharmaceutical composition comprises a buffer at a desired pH, and further comprises sucrose and a polysorbate, e.g., about 6% sucrose and about 0.01% polysorbate 80, e.g., about 10% sucrose and about 0.05% polysorbate 20. In some aspects, the pharmaceutical composition comprises a buffer at a desired pH, and further comprises sucrose, arginine, and a polysorbate, e.g., about 10% sucrose, about 50 mM arginine, and about 0.05% polysorbate 20. In some aspects, the pharmaceutical composition comprises a buffer at a desired pH, and further comprises arginine and polysorbate, e.g., about 50 mM arginine and about 0.05% polysorbate 20. In some aspects, the pharmaceutical composition comprises a buffer at a desired pH, and further comprises sodium chloride, sucrose, arginine, and polysorbate, e.g., about 75 mM NaCl, about 5% sucrose, about 50 mM arginine, and about 0.05% polysorbate 20.

In some aspects, a pharmaceutical composition comprises a humanized anti-SFRP2 antibody or antigen-binding fragment thereof as described herein, and a pharmaceutically acceptable carrier (see, e.g., Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)). Pharmaceutical compositions described herein are, in some aspects, for use as a medicament. The compositions to be used for in viva administration can be sterile. This is readily accomplished by filtration through, e.g., sterile filtration membranes.

A pharmaceutical composition described herein can be used to exert a biological effect(s) in vivo or in vitro. For example, a pharmaceutical composition described herein can be used to selectively induce apoptosis of SFRP2-expressing osteosarcoma cells e.g., the humanized anti-SFRP2 antibodies do not induce apoptosis in T-cells but do induce apoptosis of osteosarcoma cells; reduce the amount of SFRP2 in a cell; reduce the serum level of SFRP2 in a treated subject; reduce the metastatic osteosarcoma growth in a subject; reduce the amount of osteosarcoma lung metastases in a patient; reduce the amount of CD38 protein in a patient; and/or treat a disease or condition in which SFRP2 is overexpressed and/or wherein SFRP2 expression or overexpression is associated with a diseased state, such as various different cancers, e.g., osteosarcoma.

In some aspects, a pharmaceutical composition provided herein is used to treat diseases or conditions such as cancer. Examples of cancers that can be treated as provided herein include but are not limited to breast cancer, angiosarcoma, osteosarcoma, rhabdomyosarcoma, alveolar soft part sarcoma, malignant glioma, multiple myeloma, renal cell carcinoma, prostate cancer, lung cancer, and melanoma. In some aspects, a cancer may be an early stage cancer or a late stage cancer. In some aspects, a cancer is a primary tumor.

6.9 Uses and Methods

In various aspects, provided herein are in vitro and in vivo methods of using humanized anti-SFRP2 antibodies or antigen-binding fragments thereof as described herein, or pharmaceutical compositions thereof as described herein. Such methods include induction of apoptosis of SFRP2-expressing osteosarcoma cells e.g., the humanized anti-SFRP2 antibodies do not induce apoptosis in T-cells but do induce apoptosis of osteosarcoma cells: reduction of the amount of SFRP2 in a cell; reduce the serum level of SFRP2 in a treated subject; reduction of the metastatic osteosarcoma growth in a subject: reduction of the amount of osteosarcoma lung metastases in a patient; reduction of the amount of CD38 protein in a patient; and/or treatment a disease or condition in which SFRP2 is overexpressed and/or wherein SFRP2 expression or overexpression is associated with a diseased state, such as various different cancers, e.g., osteosarcoma.

In some aspects, provided herein are methods for treating cancer. In some aspects, treatment of cancer comprises: reducing the amount of SFRP2 in a cell by contacting said cell with a humanized anti-SFRP2 antibody or antigen binding fragment thereof or a pharmaceutical composition thereof as described herein: reducing the serum SFRP2 level of a patient by administering to said patient a therapeutically effective amount of a humanized anti-SFRP2 antibody or antigen binding fragment thereof or a pharmaceutical composition thereof as described herein; selectively inducing apoptosis of osteosarcoma cells in a patient, e.g., the humanized anti-SFRP2 antibodies do not induce apoptosis in T-cells but do induce apoptosis of osteosarcoma cells by administering a humanized anti-SFRP2 antibody or antigen binding fragment thereof as described herein or a pharmaceutical composition thereof; reduction of metastatic osteosarcoma growth in a patient by administering to said patient a therapeutically effective amount of a humanized anti-SFRP2 antibody or antigen binding fragment thereof as described herein or a pharmaceutical composition thereof, reducing the amount of osteosarcoma lung metastases in a patient by administering to said patient a therapeutically effective amount of a humanized anti-SFRP2 antibody or antigen binding fragment thereof or a pharmaceutical composition thereof as described herein: reducing the amount of CD38 protein in a patient by administering to said patient a therapeutically effective amount of a humanized anti-SFRP2 antibody or antigen binding fragment thereof as described herein or a pharmaceutical composition thereof; treating a patient diagnosed with osteosarcoma by administering to said patient a therapeutically effective amount of a humanized anti-SFRP2 antibody or antigen binding fragment thereof as described herein or a pharmaceutical composition thereof. In some aspects, the treatment is a monotherapy treatment comprising treatment with a humanized anti-SFRP2 antibody or antigen binding fragment thereof as described herein or a pharmaceutical composition thereof. In some aspects, treatment comprises combination therapy comprising treatment with a humanized anti-SFRP2 antibody or antigen binding fragment thereof as described herein and an antagonist of an inhibitory immune checkpoint molecule, optionally wherein the immune checkpoint molecule is PD-1 or a pharmaceutical composition thereof. In some aspects, a cancer to be treated by the methods of the present invention is a cancer with increased SFRP2 (e.g. increased SFRP2mRNA and/or increased SFRP2 protein). In some aspects, the cancer is osteosarcoma.

Furthermore, in some aspects, provided herein are methods of treating cancer, wherein the cancers to be treated by the methods described herein include but are not limited to a breast cancer, a malignant glioma, a multiple myeloma, a renal cell carcinoma, a kidney cancer, a prostate cancer, a lung cancer, a melanoma, a non-small cell lung cancer, a pancreatic cancer, a colorectal cancer, a bladder cancer, a hepatocellular carcinoma, a gastrointestinal cancer, and a sarcoma including, but not limited to an angiosarcoma, an osteosarcoma, a rhabdomyosarcoma, and an alveolar soft part sarcoma. In some aspects, a cancer may be an early stage cancer or a late stage cancer. In some aspects, a cancer is a primary tumor. In some aspects, the cancer is a cancer in which SFRP2 expression levels, e.g., SFRP2 overexpression compared to a normal state, are indicative of a diseased and/or cancerous state. In some aspects, treatment of the cancer comprises: reducing the amount of SFRP2 in a cell by contacting said cell with a humanized anti-SFRP2 antibody or antigen binding fragment thereof or a pharmaceutical composition thereof as described herein; reducing the serum SFRP2 level of a patient by administering to said patient a therapeutically effective amount of a humanized anti-SFRP2 antibody or antigen binding fragment thereof or a pharmaceutical composition thereof as described herein; selectively inducing apoptosis of cancerous cells in a patient, e.g., the humanized anti-SFRP2 antibodies do not induce apoptosis in T-cells but do induce apoptosis of cancerous cells by administering a humanized anti-SFRP2 antibody or antigen binding fragment thereof as described herein or a pharmaceutical composition thereof; reduction of metastatic cancer growth in a patient by administering to said patient a therapeutically effective amount of a humanized anti-SFRP2 antibody or antigen binding fragment thereof as described herein or a pharmaceutical composition thereof; reducing the amount of metastases, e.g., lung metastases, in a patient by administering to said patient a therapeutically effective amount of a humanized anti-SFRP2 antibody or antigen binding fragment thereof or a pharmaceutical composition thereof as described herein; reducing the amount of CD38 protein in a patient by administering to said patient a therapeutically effective amount of a humanized anti-SFRP2 antibody or antigen binding fragment thereof as described herein or a pharmaceutical composition thereof; treating a patient diagnosed with cancer by administering to said patient a therapeutically effective amount of a humanized anti-SFRP2 antibody or antigen binding fragment thereof as described herein or a pharmaceutical composition thereof; reducing the amount of proliferating cancerous cells in a patient in need thereof by administering to said patient a therapeutically effective amount of a humanized anti-SFRP2 antibody or antigen binding fragment thereof or a pharmaceutical composition thereof as described herein; increasing the amount necrotic cancerous cells in a patient in need thereof by administering to said patient a therapeutically effective amount of a humanized anti-SFRP2 antibody or antigen binding fragment thereof or a pharmaceutical composition thereof as described herein; reducing the volume of a tumor or tumors in a patient in need thereof by administering to said patient a therapeutically effective amount of a humanized anti-SFRP2 antibody or antigen binding fragment thereof or a pharmaceutical composition thereof as described herein; selectively reducing PD-1 levels in T-cells in a patient in need thereof by administering to said patient a therapeutically effective amount of a humanized anti-SFRP2 antibody or antigen binding fragment thereof or a pharmaceutical composition thereof as described herein. In some aspects, the treatment is a monotherapy treatment comprising treatment with a humanized anti-SFRP2 antibody or antigen binding fragment thereof as described herein or a pharmaceutical composition thereof. In some aspects, treatment comprises combination therapy comprising treatment with a humanized anti-SFRP2 antibody or antigen binding fragment thereof as described herein and an antagonist of an inhibitory immune checkpoint molecule, optionally wherein the immune checkpoint molecule is PD-1 or a pharmaceutical composition thereof. In some aspects, a cancer to be treated by the methods of the present invention is a cancer with increased SFRP2 (e.g. increased SFRP2 mRNA and/or increased SFRP2 protein).

In some aspects, a method of treating a cancer is provided, e.g., breast cancer, angiosarcoma, osteosarcoma, rhabdomyosarcoma, alveolar soft part sarcoma, malignant glioma, multiple myeloma, renal cell carcinoma, prostate cancer, lung cancer, or melanoma, wherein the method comprises administering a humanized anti-SFRP2 antibody or antigen-binding fragment thereof, or pharmaceutical composition thereof, and wherein the method further comprises administering an antagonist of an inhibitory immune checkpoint molecule. In some aspects, the antagonist of inhibitory checkpoint molecule is PD-1 (programmed cell death protein-1). In some aspects, an antagonist of PD-1 is an antibody to PD-1. PD-1 antibodies include, for example, OPDIVO (nivolumab), KEYTRUDA (pembrolizumab), MEDI-0680 (AMP-514; WO2012/145493), camrelizumab (SHR-1210), tislelizumab (BGB-A317), or spartalizumab (NPVPDR001, NVS240118, PDR001). A recombinant protein composed of the extracellular domain of PD-L2 (B7-DC) fused to the Fc portion of IgG1, called AMP-224, can also be used to antagonize the PD-1 receptor. In some aspects, a humanized anti-SFRP2 antibody or antigen-binding fragment thereof, or pharmaceutical composition thereof, is administered in combination with radiation therapy and/or a chemotherapeutic agent.

6.10 Administration and Dosing

A humanized SFRP2 antibody or antigen-binding fragment thereof as provided herein, or a pharmaceutical composition thereof as provided herein, can be administered by any suitable means, including parenteral, intrapulmonary, intranasal, intratumoral, intralesional administration, intracerebrospinal, intracranial, intraspinal, intrasynovial, intrathecal, oral, topical, or inhalation routes. Parenteral infusions include intramuscular, intravenous administration as a bolus or by continuous infusion over a period of time, intraarterial, intra-articular, intraperitoneal, or subcutaneous administration. In some aspects, the administration is intravenous administration. In some aspects, the administration is subcutaneous.

The appropriate dosage and dosing regimen of a humanized anti-SFRP2 antibody or antigen-binding fragment thereof as provided herein, or a pharmaceutical composition thereof as provided herein, when used alone or in combination with one or more other additional therapeutic agents, e.g., one or more antagonists of inhibitory immune checkpoint molecules, will depend on the disease to be treated, the severity and course of the disease, the route of administration and other factors.

In some aspects, the humanized anti-SFRP2 antibody or antigen binding fragment thereof is administered, e.g., to a patient in need thereof in an amount of from 0.1 mg/kg body weight to 200 mg/kg body weight, e.g., from 0.1 mg/kg body weight to about 100 mg/kg body weight, e.g., about 1-30 mg/kg body weight, e.g., about 5-15 mg/kg body weight. In some aspects, the humanized anti-SFRP2 antibody or antigen binding fragment thereof is administered in an amount of 0.1 mg/kg body weight or less, 0.25 mg/kg body weight or less, 0.50 mg/kg body weight or less, 0.75 mg/kg body weight or less, 1 mg/kg body weight or less, 2 mg/kg body weight or less, 3 mg/kg body weight or less, 4 mg/kg body weight or less, 5 mg/kg body weight or less, 6 mg/kg body weight or less, 7 mg/kg body weight or less, 8 mg/kg body weight or less, 9 mg/kg body weight or less, 10 mg/kg body weight or less, 15 mg/kg body weight or less, 20 mg/kg body weight or less, 25 mg/kg body weight or less, 30 mg/kg body weight or less, 35 mg/kg body weight or less, 40 mg/kg body weight or less, 45 mg/kg body weight or less, 50 mg/kg body weight or less, 60 mg/kg body weight or less, 70 mg/kg body weight or less, 80 mg/kg body weight or less, 90 mg/kg body weight or less, 100 mg/kg body weight or less, or 200 mg/kg body weight or less. In some aspects, the humanized anti-SFRP2 antibody or antigen binding fragment thereof is administered in an amount of from about 0.1 mg/kg body weight to about 100 mg/kg body weight, about 0.5 mg/kg body weight to about 50 mg/kg body weight, about 1.0 mg/kg body weight to about 40 mg/kg body weight, about 1.0 to about 30.0 mg/kg body weight, about 1.0 mg/kg body weight to about 25 mg/kg body weight, about 1.0 mg/kg body weight to about 20 mg/kg body weight, about 1.0 mg/kg body weight to about 15 mg/kg body weight, about 2.0 to about 30 mg/kg body weight, about 2.0 to about 25 mg/kg body weight, about 2.0 to about 20 mg/kg body weight, about 2.0 to about 15 mg/kg body weight, about 3.0 to about 30 mg/kg body weight, about 3.0 to about 25 mg/kg body weight, about 3.0 to about 20 mg/kg body weight, about 3.0 to about 15 mg/kg body weight, about 4.0 to about 30 mg/kg body weight, about 4.0 to about 25 mg/kg body weight, about 4.0 to about 20 mg/kg body weight, about 4.0 to about 15 mg/kg body weight, about 5.0 to about 30 mg/kg body weight, about 5.0 to about 25 mg/kg body weight, about 5.0 to about 20 mg/kg body weight, or about 5.0 to about 15 mg/kg body weight.

In some aspects, the humanized anti-SFRP2 antibody or antigen binding fragment thereof is administered, e.g., to a patient in need thereof, as a part of a combination therapy in an amount described herein. In some aspects, the combination therapy comprises one or more antagonists of inhibitory immune checkpoint molecules, e.g., one or more PD-1 inhibitors. In some aspects, the combination therapy comprises one or more PD-1 inhibitors, wherein the inhibitor is administered in an amount of from 0.1 mg/kg body weight to 200 mg/kg body weight, e.g., from 0.1 mg/kg body weight to about 100 mg/kg body weight. In some aspects, the one or more PD-1 inhibitors are administered in an amount of 0.1 mg/kg body weight or less, 0.25 mg/kg body weight or less, 0.50 mg/kg body weight or less, 0.75 mg/kg body weight or less, 1 mg/kg body weight or less, 2 mg/kg body weight or less, 3 mg/kg body weight or less, 4 mg/kg body weight or less, 5 mg/kg body weight or less, 6 mg/kg body weight or less, 7 mg/kg body weight or less, 8 mg/kg body weight or less, 9 mg/kg body weight or less, 10 mg/kg body weight or less, 15 mg/kg body weight or less, 20 mg/kg body weight or less, 25 mg/kg body weight or less, 30 mg/kg body weight or less, 35 mg/kg body weight or less, 40 mg/kg body weight or less, 45 mg/kg body weight or less, 50 mg/kg body weight or less, 60 mg/kg body weight or less, 70 mg/kg body weight or less, 80 mg/kg body weight or less, 90 mg/kg body weight or less, 100 mg/kg body weight or less, or 200 mg/kg body weight or less. In some aspects, the one or more PD-1 inhibitors are administered in an amount of from about 0.1 mg/kg body weight to about 20 mg/kg body weight, about 0.5 mg/kg body weight to about 15 mg/kg body weight, about 1.0 mg/kg body weight to about 10 mg/kg body weight, about 2.0 mg/kg body weight to about 10.0 mg/kg body weight, about 3.0 mg/kg body weight to about 10.0 mg/kg body weight, about 4.0 mg/kg body weight to about 10.0 mg/kg body weight, about 5.0 mg/kg body weight to about 10.0 mg/kg body weight, about 6.0 mg/kg body weight to about 10.0 mg/kg body weight, about 7.0 mg/kg body weight to about 10.0 mg/kg body weight, about 7.5 mg/kg body weight to about 10 mg/kg body weight, or about 8.0 mg/kg body weight to about 10 mg/kg body weight body weight.

In some aspects, the PD-1 antagonist is administered daily, once every 3 days, once every week, once every 2 weeks, once every 3 weeks, once every 4 weeks, once every 6 weeks, once every 8 weeks, or once every 12 weeks.

In some aspects, the humanized anti-SFRP2 antibody or antigen binding fragment thereof and the one or more PD-1 inhibitors are administered for at least 3 days, for at least 30 days, for at least 42 days, for at least 8 weeks, for at least 12 weeks, for at least 24 weeks, for at least 6 months, or for at least 12 months or until cancer recurs.

In some aspects, the humanized anti-SFRP2 antibody or antigen binding fragment thereof are administered two or more times with an interval between the two administrations. In some aspects, the interval is at least about an hour, at least about 12 hours, at least about a day, at least about two days, at least about three days, at least about four days, at least about five days, at least about six days, at least about one week, at least about two weeks, at least about three weeks, at least about four weeks, at least about a month, at least about five weeks, at least about six weeks, at least about seven weeks, at least about eight weeks, at least about two months, at least about nine weeks, at least about ten weeks, at least about eleven weeks, at least about twelve weeks, at least about three months, at least about six months, or at least about twelve months. In some aspects, the interval is about an hour, about 12 hours, about a day, about two days, about three days, about four days, about five days, about six days, about a week, about two weeks, about three weeks, about four weeks, about a month, about five weeks, about six weeks, about seven weeks, about eight weeks, about two months, about nine weeks, about 10 weeks, about 11 weeks, about 12 weeks, about three months, about six months, or about twelve months. In some aspects, the interval is the same throughout the doses. In some aspects, the interval is different throughout the doses.

In some aspects, the humanized anti-SFRP2 antibody or antigen-binding fragment thereof are administered as a combination therapy comprising one or more antagonists of inhibitory immune checkpoint molecules, e.g., one or more PD-1 inhibitors. In some aspects, the humanized anti-SFRP2 antibody or antigen binding fragment thereof and the one or more antagonists of inhibitory immune checkpoint molecules are administered simultaneously, separately, or sequentially. In some aspects, the humanized anti-SFRP2 antibody or antigen-binding fragment thereof is administered first, and the one or more inhibitory immune checkpoint molecules are administered after an interval of time. In some aspects, one or more antagonists of inhibitory immune checkpoint molecules are administered first, and the humanized anti-SFRP2 antibody or antigen-binding fragment thereof are administered after an interval of time. In some aspects, the interval is at least about an hour, at least about 12 hours, at least about a day, at least about two days, at least about three days, at least about four days, at least about five days, at least about six days, at least about one week, at least about two weeks, at least about three weeks, at least about four weeks, at least about a month, at least about five weeks, at least about six weeks, at least about seven weeks, at least about eight weeks, at least about two months, at least about nine weeks, at least about ten weeks, at least about eleven weeks, at least about twelve weeks, at least about three months, at least about six months, or at least about twelve months. In some aspects, the interval is about an hour, about 12 hours, about a day, about two days, about three days, about four days, about five days, about six days, about a week, about two weeks, about three weeks, about four weeks, about a month, about five weeks, about six weeks, about seven weeks, about eight weeks, about two months, about nine weeks, about 10 weeks, about 11 weeks, about 12 weeks, about three months, about six months, or about twelve months. In some aspects, the interval is the same throughout the doses. In some aspects, the interval is different throughout the doses.

In some aspects, the humanized anti-SFRP2 antibody or antigen binding fragment thereof is administered, e.g., to a patient in need thereof, as a part of a combination therapy which optionally comprises administration of one or more antagonists of inhibitory immune checkpoint molecules, wherein the combination therapy further comprises radiation therapy, chemotherapy, cytokine therapy, and/or gene therapy.

In some aspects, provided herein is a humanized anti-SFRP2 antibody or antigen-binding fragment thereof or pharmaceutical composition provided herein for use as a medicament.

In some aspects, provided herein is a humanized anti-SFRP2 antibody or antigen-binding fragment thereof or pharmaceutical composition provided herein, for use in a method for the treatment of cancer, e.g., osteosarcoma. In some aspects, provided herein is a humanized anti-SFRP2 antibody or antigen-binding fragment thereof or pharmaceutical composition provided herein, for use in a method for the treatment of cancer in a subject, comprising administering to the subject an effective amount of a humanized anti-SFRP2 antibody or antigen-binding fragment thereof or pharmaceutical composition provided herein.

8. EXAMPLES

Example 1: Preparation of Humanized Anti-SFRP2 Antibodies

In the present example, humanized anti-SFRP2 antibodies were prepared as follows. First, sequencing of the variable heavy chain and variable light chain regions was performed on murine anti-SFRP2 antibody variable region genes obtained from an anti-SFRP2 hybridoma of the Mo.1 antibody (VH chain of SEQ ID NO: 10; VL chain of SEQ ID NO: 11). Following sequencing, the sequence information was used to design a series of humanized antibody variants. Composite V region genes were generated using synthetic oligonucleotides encoding combinations of selected human sequence segments. VH and VL chain constructs were then cloned into vectors containing either IgG1 heavy chains or kappa light chains. The amino acid sequences and sequence identifiers of the variable heavy chain and variable light chain regions cloned into vectors are presented in Table 1 and Table 2 below.

TABLE 1

| VH CHAIN AMINO ACID SEQUENCES | |
|---|---|
| SEQ ID NO | AMINO ACID SEQUENCE |
| 1 | QVQLVQSGAELKKPGASVKVSCKASGFTFTRYWWHWVRQAPGKGLEWI GRIDPNSGTTRFIEKFKTRATITVDKSTSTAYMHLSSLRSEDSAVYYCARW GPYYGYAMDYWGQGTSVTVSS |
| 2 | QVQLVQSGAELKKPGASVKVSCKASGFTFTRYWWHWVRQAPGKGLEWI GRIDPNSGTTRFIEKFKTRATITVDKSTSTAYMELSSLRSEDSAVYYCARW GPYYGYAMDYWGQGTSVTVSS |
| 3 | QVQLVQSGAEVKKPGASVKVSCKASGFTFTRYWWHWVRQAPGKGLEWI GRIDPNSGTTRFIEKFKTRATITVDKSTSTAYMELSSLRSEDTAVYYCARW GPYYGYAMDYWGQGTLVTVSS |
| 4 | QVQLVQSGAEVKKPGASVKVSCKASGFTFTRYWWHWVRQAPGKGLEWI GRIDPNSGTTRFIEKFKTRVTITVDKSTSTAYMELSSLRSEDTAVYYCARW GPYYGYAMDYWGQGTLVTVSS |

TABLE 2

| VL CHAIN AMINO ACID SEQUENCES | |
|---|---|
| SEQ ID NO | AMINO ACID SEQUENCE |
| 5 | QIVLTQSPAILSLSPGERVTITCSASSSVTYMHWYQQKLGKAPKLWIYDTS RLAPGSPARFSGSGSGTDYTLTISSLETEDFASYFCHQWSTYPPTFGQGTKL EIK |

TABLE 2-continued

VL CHAIN AMINO ACID SEQUENCES

| SEQ ID NO | AMINO ACID SEQUENCE |
|---|---|
| 6 | QIVLTQSPATLSLSPGERVTITCSASSSVTYMHWYQQKLGKAPKLWIYDTSRLAPGSPARFSGSGSGTDYTLTISSLESEDFASYFCHQWSTYPPTFGQGTKLEIK |
| 7 | QIVLTQSPATLSLSPGERVTITCSASSSVTYMHWYQQKPGKAPKLWIYDTSRLAPGSPARFSGSGSGTDYTLTISSLESEDFASYFCHQWSTYPPTFGQGTKLEIK |
| 8 | QIVLTQSPATLSLSPGERVTITCSASSSVTYMHWYQQKPGKAPKLWIYDTSRLAPGSPARFSGSGSGTDYTLTISSLESEDFATYFCHQWSTYPPTFGQGTKLEIK |
| 9 | QIVLTQSPATLSLSPGERVTITCSASSSVTYMHWYQQKPGKAPKLLIYDTSRLAPGSPARFSGSGSGTDYTLTISSLESEDFATYFCHQWSTYPPTFGQGTKLEIK |

Each possible combination of VH and VL chains, i.e., 20 total pairings, were stably transfected into NS0 cells via electroporation for expression testing. These combinations are presented in Table 3 below.

TABLE 3

| VH/VL Chain Combination | Antibody Identifier |
|---|---|
| SEQ ID NO: 1 and SEQ ID NO: 6 | Ab1 |
| SEQ ID NO: 1 and SEQ ID NO: 7 | Ab2 |
| SEQ ID NO: 1 and SEQ ID NO: 8 | Ab3 |
| SEQ ID NO: 1 and SEQ ID NO: 9 | Ab4 |
| SEQ ID NO: 2 and SEQ ID NO: 6 | Ab5 |
| SEQ ID NO: 2 and SEQ ID NO: 7 | Ab6 |
| SEQ ID NO: 2 and SEQ ID NO: 8 | Ab7 |
| SEQ ID NO: 2 and SEQ ID NO: 9 | Ab8 |
| SEQ ID NO: 3 and SEQ ID NO: 6 | Ab9 |
| SEQ ID NO: 3 and SEQ ID NO: 7 | Ab10 |
| SEQ ID NO: 4 and SEQ ID NO: 8 | Ab11 |
| SEQ ID NO: 4 and SEQ ID NO: 9 | Ab12 |
| SEQ ID NO: 3 and SEQ ID NO: 5 | Ab13 |
| SEQ ID NO: 3 and SEQ ID NO: 9 | Ab14 |
| SEQ ID NO: 1 and SEQ ID NO: 5 | Ab15 |
| SEQ ID NO: 2 and SEQ ID NO: 5 | Ab16 |
| SEQ ID NO: 4 and SEQ ID NO: 5 | Ab17 |
| SEQ ID NO: 3 and SEQ ID NO: 8 | Ab18 |
| SEQ ID NO: 4 and SEQ ID NO: 6 | Ab19 |
| SEQ ID NO: 4 and SEQ ID NO: 7 | Ab20 |

Successful transfection and stable clone selection were achieved for the majority of VH and VL chain combinations evaluated; however, some chain combinations, for example, some of those containing VK1, did not provide clones (e.g. VH1/VK1, VH2/VK1, and VH4/VK1).

The various different antibodies expressed from the NS0 cells were purified from cell culture supernatants on a Protein A sepharose column (GE Healthcare), buffer exchanged into PBS pH 7.4, and analyzed by reducing SDS-PAGE (see FIG. 1A). Bands corresponding to the predicted sizes of the VH and VL chain polypeptides were observed in each case (see FIG. 1A). The lanes of the SDS-PAGE gel were loaded as follows: 1=MW marker; 2=Ab1; 3=Ab2; 4=Ab3; 5=Ab4; 6=Ab5; 7=Ab6; 8=Ab7; 9=Ab8; 10=Ab9; 11=MW marker; 12=MW marker; 13=Ab10; 14=Ab11; 15=Ab12; 16=MW marker; 17=Ab13; and Lane 18=Ab14 (see FIG. 1A).

In addition to the humanized antibodies Ab1-Ab20 discussed supra, two chimeric antibodies, Chi.1 and Chi.2, were prepared as follows. Mo.1 VH and VL chains (SEQ ID NOs: 10 and 11, respectively) were cloned into IgG1 VH and VK chain expression vectors. Chi.1 antibody was produced first and sequenced. Upon sequencing, it was noted that Chi.1 comprised a lysine at Kabat position 106a, whereas Mo.1 comprised a glutamine at Kabat position 106a. As such, a second chimeric antibody, Chi.2, was prepared which comprised a glutamine at position 106a Kabat. The one residue difference at Kabat position 106a was not found to affect binding of the chimeric antibody to SFRP2 (data not shown). The VH chain and VL chain of Chi.1 comprised the amino acid sequences of SEQ ID NO: 10 and SEQ ID NO: 11, respectively. The VH chain and VL chain of Chi.2 comprised the amino acid sequences of SEQ ID NO: 10 and SEQ ID NO: 13, respectively.

Chi.1 and Chi.2 independently expressed in HEK and NS0 cells were purified from cell culture supernatants on a Protein A sepharose column (GE Healthcare), buffer exchanged into PBS pH 7.4, and analyzed by reducing SDS-PAGE (see FIG. 1B). Bands corresponding to the predicted sizes of the VH and VL chain polypeptides were observed in each case (see FIG. 1B). The lanes of the SDS-PAGE gel were loaded as follows: 1=MW marker; 2=Chi.1 purified from HEK cells; 3=Chi.2 purified from HEK cells; 4=MW marker; 5=Chi.1 purified from NS0 cells; 6=Chi.2 purified from NS0 cells. No significant differences in expression or purity of Chi.1, as compared to Chi.2 were noted.

Example 2: Comparative Analysis of Anti-SFRP2 Antibodies

In the present example, antibodies Ab1-Ab14 prepared as in Example 1 were subjected to comparative analysis. Furthermore, Ab1-Ab14 were compared to the parental murine antibody, Mo.1, which antibody binds to SFRP2 (SEQ ID NO: 12). The murine antibody Mo.1 comprised the VH chain polypeptide sequence of SEQ ID NO: 10 and the VL chain polypeptide sequence of SEQ ID NO: 11.

To compare the performance of each of the various different antibody constructs to one another and to Mo.1, each of antibodies Ab1-Ab14 and Mo.1 were evaluated in a competition binding assay (ELISA). Briefly, a dilution series (three-fold) of each of Ab1-Ab14 from 10 µg/ml to 0.0046 µg/ml was premixed with a constant concentration of biotinylated Mo.1 antibody (0.16 µg/ml, final concentration) before incubating for 1 hour at room temperature on a NUNC IMMUNO MAXISORP™ 96 well flat bottom microtitre plate pre-coated with a 1/5000 dilution of Peptide B (SEQ ID NO: 14) diluted in carbonate buffer. The binding of the biotinylated antibody was detected with streptavidin-HRP and TMB substrate.

The results obtained from the competitive ELISA analysis were used to calculate $IC_{50}$ values for each antibody, which values were normalized to the $IC_{50}$ value of the mouse Mo.1 antibody that was included on each ELISA plate. The relative $IC_{50}$ values that were obtained are presented in FIG. 2. As can been observed from the IC50 values that were obtained, all of the tested antibodies, i.e., Ab1-Ab14, demonstrated improved binding to SFRP2/Peptide B as compared to the murine antibody Mo.1.

To further evaluate antibody performance, each of antibodies Ab1-Ab14 were evaluated in an endothelial tube formation assay. Briefly, 2H11 mouse endothelial cells (#CRL-2163, ATCC®, Manassas, VA, USA) were cultured in Opti-MEM (#22600134, Thermo Fisher Scientific, Waltham, MA, USA) with 5% heat-inactivated fetal bovine serum (FBS, #FB-12, Omega Scientific, Biel/Bienne, Switzerland) and 1% penicillin/streptomycin (v/v). The cells were cultured at 37° C. in a humidified 5% CO2-95% room air atmosphere. The cultured 2H11 endothelial cells were then plated in Opti-MEM with 5% FBS and allowed to settle for 24 hrs. Quiescence was induced by maintaining the cells in Opti-MEM with 2.5% FBS overnight. Matrigel™ (#ECM625, Millipore, Bedford, MA, USA) was polymerized in the wells of a 96-well plate according to the In Vitro Angiogenesis Assay protocol (#ECM625 Millipore). In this assay, an IgG1 control (5 uM) was compared to samples which were each independently treated with one of Ab1-Ab14 at increasing concentrations of 0.5, 1, 5, 10, or 20 uM for each antibody. Each sample, aside from a negative control that was treated with only IgG1, was treated with 30 nM SFRP2, which promoted tube formation. A positive control was treated with both IgG1 and SFRP2. Treatments resuspended in Opti-MEM with 2.5% FBS were pre-incubated on a rocker at 37° C. 5% $CO_2$, for 90 minutes prior to adding them to the cells. $1.9 \times 10^4$ cells were resuspended in 150 ml of pre-incubated treatments, then incubated for an additional 30 min on a rocker at 37° C., 5% $CO_2$. Finally, the cell suspension was added to each well previously coated with polymerized Matrigel™ Control cells were given fresh Opti-MEM with 2.5% FBS and 5 mM IgG1. For each treatment condition, after 4h of incubation at 37° C. 5% CO2, images were acquired using the 4× objective lens of the EVOS FL Digital Imaging System (Thermo Fisher Scientific, Waltham, MA, USA).

Referring now to FIG. 3, FIG. 3 presents representative results of the assay for the control assay (see 1 of FIG. 3) as well as treatment with Ab8 (see 2 of FIG. 3) or treatment with Ab11 (see 3 of FIG. 3). As can be observed in the images of FIG. 3. Ab8 and Ab11 both significantly reduced the number of endothelial branch points as compared to the control.

Antibody performance was further evaluated in a tube formation assay using SVR angiosarcoma cells. Briefly. SVR angiosarcoma cells were plated in Matrigel at 12.000 cells/well and were treated with either control, Ab2, Ab3, Ab8, Ab11, or Ab 12 at 100 ng/μl (n=4 per group). After 4 hours a picture of the tubes in the well under the microscope is taken and branch points counted by Image J. This is done by using the mouse to click on each branch point in the image. A colored number corresponding to the type that is counted is be displayed on the image after every click, and the corresponding counter is updated and counts all of the branch points on the image.

Referring now to FIG. 9A, FIG. 9A presents representative results of the assay for the control treatment (see 1 of FIG. 9A) as well as treatment with Ab1 (see 2 of FIG. 9A) or treatment with Ab8 (see 3 of FIG. 9A). As can be observed in the images of FIG. 9A, Ab8 significantly reduced the number of endothelial branch points as compared to both Ab11 and the control.

Referring now to FIG. 9B, the data obtained from the above tube formation assays is presented as percent inhibition (treated/control)×100. A two-tailed T-test was performed with P<0.05 being significant. The results of the formation assay were quantified as percent inhibition (treated/control)×100. As can be observed in FIG. 9B, treatment with Ab8 was the only treatment that significantly inhibited tube formation as compared to the control (*p=0.03).

Example 3: Humanized Anti-SFRP2 Antibodies Selectively Induce Apoptosis in Osteosarcoma Cells but not T Cells In the present example, the effect of a humanized anti-SFRP2 antibody, Ab8, on the treatment of RF577 osteosarcoma cells was measured. Furthermore, the effects of a humanized anti-SFRP2 antibody Ab8 on T-cell apoptosis was measured.

For the RF577 cell line assay. RF577 cell line, which expresses SFRP2 endogenously, was plated in 96 well plates (#0030730119; Eppendorf, Hamburg, Germany) at $1.0 \times 10^4$ cells/well. The next day, cells were treated for 1h with 10 μM of Ab8, or 10 μM of IgG1 control, at 37° C., 5% $CO_2$. Apoptosis was measured following the protocol of the Apoptotic Detection kit (#PK-CA707-30017; PromoCell, GmbH, Heidelberg, Germany). Apoptotic cells were positive for FITC and necrotic cells were positive for Texas Red. Images were acquired using the 10× objective lens of the EVOS FLc Digital Imaging System (Thermo Fisher Scientific). Cells were counted using ImageJ cell counting software. Each data point was the result of 3 independent experiments, each containing 4 separate wells (n=12).

Referring now to FIG. 4A, the percentage of apoptotic cells after treatment with Ab8 increased significantly. In the RF577 cells, Ab8 increased apoptosis to 52.4±0.08% from 11.8±0.3% in the IgG treated cells (n=12, **p<0.0001) (see FIG. 4A).

For the T-cell apoptosis assay, splenocytes isolated from C57bl6 mice were stimulated for 48 hours in TCR and 6000 U/mL IL-2. Following stimulation, the splenocytes were then removed from wells, washed twice with PBS, and CD4+/CD8+ T cells were selected by negative subtraction using the following mix of biotinylated antibodies diluted at 1:200: TER119 (#116204), CD25 (#102004), OR-1 (#108404), NK1.1 (#108704), CD11C (#117304), CD11B (#101204), CD19 (#101504), all from BioLegend (San Diego, CA, USA), and subsequently incubated on ice for 15 min. Cells were then incubated for 20 min RT on a magnetic tube holder with 200 μL of streptavidin-bound beads solution (#557812) from BD Biosciences (Franklin Lakes, NJ, USA). CD4+ and CD8+ cells were isolated from the supernatant and other cells bound to the beads were discarded.

To measure the effect of Ab8 on T-cell apoptosis. T-cells (CD4$^+$ and CD8$^+$) were isolated as described above, treated with IgG1 (10 μM) or Ab8 (10 μM) for 24h. stained for Hoechst and Annexin V, and then analyzed by flow cytometry. A positive control for apoptosis was obtained from T-cells passed through various freeze/thaw cycles in DMSO-containing medium that was used for the experiment. The percentage of apoptotic cells in the IgG1 control-treated samples was significantly lower than in the positive control group (n=3, *p<0.001) (see FIG. 4B). Compared to the IgG1 treated samples, the percentage of apoptotic cells remained unchanged in the Ab8-treated samples (n=3, p=NS) (see FIG. 4B).

Example 4: Monotherapy and Combination Therapy Comprising Humanized Anti-SFRP2 Antibodies Reduces SFRP2 Serum Levels In the present example, the effects of mono- and combination therapies comprising use of humanized anti-SFRP2 antibody Ab8 were evaluated for reduction of SFRP2 serum levels.

Blood from C57BL6 control mice (n=3) or RF577-bearing mice treated with IgG1 (n=9), Ab8 (n=12), PD-1 mAb (n=8) (an anti-mouse PD-1:CD279 monoclonal antibody purchased from Bioxcell, Lebanon, NH USA (#BE0273)), or a combination of both antibodies (n=12) was collected from the inferior vena cava immediately after euthanasia and laparotomy. Separation of serum was performed using BD Vacutainer EDTA SST tubes (#367981; Becton Dickinson and Company, Franklin Lakes, NJ, USA) following the manufacturer protocol. The serum samples were then processed using the RayBiotech Mouse SFRP2 ELISA kit (ELM-SFRP-2; Peachtree Corners, GA, USA) following the manufacturer protocol. Finally, absorbance was read at 450 nm with Synergy 2 plate reader, using Gen5 2.06 software (BioTek Instruments, Winooski, VT, USA).

Referring now to FIG. 5, ELISA was used to compare the serum levels of SFRP2 in all treatment groups of the C57/BL6 mice with metastatic RF577 OS and C57/BL6 mice without tumors. The levels of SFRP2 protein were increased in the serum of control tumor-bearing mice (n=9) compared to non-tumor bearing mice (n=8) (32.6±2.64 ng/ml vs. 9.30±2.52 ng/mL, respectively; p<0.01; FIG. 5). In addition, the levels of SFRP2 between the treatment groups (control (n=9), PD-1 mAb (n=8), Ab8 (n=12), and combination therapy (n=12)) were compared. All treatment groups had significantly lower SFRP2 levels compared to IgG control-treated mice (32.6±2.64 ng/ml for IgG control; 11.7±3.12 ng/ml for PD-1 mAb; 9.14±2.02 ng/ml for Ab8; 10.5±2.30 ng/ml for combination; p<0.01: FIG. 5).

Example 5: Treatment of Metastatic Osteosarcoma with Humanized Anti-SFRP2 Antibodies Decrease CD39 Levels In the present example, the effects of treating metastatic osteosarcoma with a humanized anti-SFRP2 antibody, Ab8, on CD38 levels was evaluated.

Mice with RF577 OS lung metastases were prepared as generally described in Example 4 above. Splenocytes were harvested from these mice at day 49 and treated with IgG1 control (n=5) or Ab8 (n=5). Following treatment, the splenocytes were lysed and prepared for Western blot analysis probing for CD38 using standard protocols. Densitometry was performed on ImageJ comparing loading controls and proteins of interest. Densities were calculated by multiplying the average intensity by the surface of each band. Loading control was used to eliminate inter-sample variability. Final results were obtained by normalizing each value to untreated controls.

Referring now to FIG. 6, mean relative CD38 protein levels normalized to actin were reduced in T-cells from mice treated with Ab8 by 82% compared to the control group treated with IgG1 (p=0.004).

Example 6: Monotherapy and Combination Therapy Comprising Humanized Anti-SFRP2 Antibodies Inhibit Osteosarcoma Lung Metastases In the present example, mono- and combination therapies, each comprising use of the humanized anti-SFRP2 antibody Ab8, were evaluated for their effects in inhibiting osteosarcoma lung metastases in in vivo models.

Osteosarcoma lung metastases were generated by tail vein injection in C57/B16 mice with 5×10$^5$ RF577 tumor cells/100 µl previously filtered and resuspended in PBS. A total of 62 mice were injected. Treatments started 12 days after tumor cell injection with either IgG1 control antibody (4 mg/kg, iv, weekly; n=13), PD-1 mAb (200 µg/100 µL ip, q3 days, n=14), Ab8 (4 mg/kg iv, q3 days, n=15), or a combination of both treatments (n=14), and continued for 49 days. After 49 days, the mice were euthanized, and their lungs removed. High-resolution photographs were taken and utilized to quantitate metastatic surface lung nodules for each treatment group. The PD-1 mAb used was an anti-mouse PD-1/CD279 monoclonal antibody purchased from Bioxecll, Lebanon, NH USA (#BE0273).

The quantification of this data is presented in FIG. 7A. Referring to FIG. 7A, of the 56 mice analyzed on day 49 of treatment, the number of surface metastases was 11.5±2.5 in the IgG1-treated group, 6.7±3 in the PD-1 mAb-treated group, 7.8±1.3 in the Ab8-treated group, and combination therapy was 4.2±1.1 (p=0.018 comparing IgG1 versus combination; see FIG. 7A). As can be observed from the data presented in FIG. 7A, the combination therapy significantly decreased lung surface metastasis compared to the IgG1 control (*p=0.018). As can be observed from the data presented in FIG. 7A, monotherapy with Ab8 also decreased lung surface metastasis compared to the IgG1 control.

In parallel with the above study, animal weights were measured starting on the first day of treatment and then weekly until the final week of treatment. The data collected are presented in FIG. 7B. As presented in FIG. 7B, no significant reduction in weight was seen in any treatment group.

A second study, similar to the above study, was performed to evaluate the effects of monotherapy and combination therapy comprising use of humanized anti-SFRP2 antibody Ab8 in treating osteosarcoma lung metastases. The study was performed generally as described above, however, in this instance the percent of mouse lung occupied by tumor was measured following harvesting of mouse lungs. This measurement was calculated by dividing the tumor area by the normal lung area multiplied by 100, and the treatments were normalized to the control. The results obtained from this study are presented in FIG. 8. As can be observed in FIG. 8, treatment with Ab8 reduced lung metastatic tumor volume compared to the control by 71%, and the combination therapy reduced the tumor volume compared to the control by 82%.

TABLE 6

Amino Acid Codes and Functionally Equivalent Codons

| Full Name | 3-Letter Code | 1-Letter Code | Functionally Equivalent Codons |
|---|---|---|---|
| Aspartic Acid | Asp | D | GAC; GAU |
| Glutamic Acid | Glu | E | GAA; GAG |
| Lysine | Lys | K | AAA; AAG |
| Arginine | Arg | R | AGA; AGG; CGA; CGC; CGG; CGU |

TABLE 6-continued

Amino Acid Codes and Functionally Equivalent Codons

| Full Name | 3-Letter Code | 1-Letter Code | Functionally Equivalent Codons |
|---|---|---|---|
| Histidine | His | H | CAC; CAU |
| Tyrosine | Tyr | Y | UAC; UAU |
| Cysteine | Cys | C | UGC; UGU |
| Asparagine | Asn | N | AAC; AAU |
| Glutamine | Gln | Q | CAA; CAG |
| Serine | Ser | S | ACG; AGU; UCA; UCC; UCG; UCU |
| Threonine | Thr | T | ACA; ACC; ACG; ACU |
| Glycine | Gly | G | GGA; GGC; GGG; GGU |
| Alanine | Ala | A | GCA; GCC; GCG; GCU |
| Valine | Val | V | GUA; GUC; GUG; GUU |
| Leucine | Leu | L | UUA; UUG; CUA; CUC; CUG; CUU |
| Isoleucine | Ile | I | AUA; AUC; AUU |
| Methionine | Met | M | AUG |
| Proline | Pro | P | CCA; CCC; CCG; CCU |
| Phenylalanine | Phe | F | UUG; UUU |
| Tryptophan | Trp | W | UGG |

Example 7: Efficacy and Biodistribution of hSFRP2 mAb in MDA-231 Human Triple Negative Breast Cancer Methods Study Design. An orthotopic model was used in nude mice with human triple negative breast cancer MDA-MB-231 cells and evaluated the in vivo kinetics of hSFRP2 mAb through treatment of hSFRP2 mAb conjugated to a NIR-fluorophore. The cellular association of the mAb was monitored by measuring the emission Dylight 755 over 72 hours with the in vivo Maestro imaging system. A NIR-tagged IgG1 control was used as a treatment control, and tumor-free mice served as healthy controls. Efficacy of the hSFRP2 mAb treatment was investigated in a separate in vivo experiment with the same orthotopic model.

Cell Culture. MDA-MB-231 cells (ATCC, Manassas, VA, USA) were cultured in DMEM (#30-202, ATCC®) with 10% heat inactivated FBS (#BT 201-500-D, BioFluid, Fleming Island, FL, USA) and 1% penicillin/streptomycin (#MT30009C, Thermo Fisher Scientific, Waltham, MA, USA) at 37° C. with 5% $CO_2$ and 95% humidity. Cells were authenticated by ATCC® and tested for rodent pathogens by Charles River Research Animal (Wilmington, MA, USA) before injection in vivo.

Antibodies and Proteins. Control IgG1 was obtained from Novartis (Basel, Switzerland) as Omalizumab (#NDC 50242-040-62). It was reconstituted per packaging and diluted with PBS to a dosage of 4 mg/kg for in vivo treatment. Humanized SFRP2 mAb (Ab8) was constructed as previously described in Example 1 and purified to remove endotoxins. It was diluted with PBS to a dosage of 4 mg/kg for in vivo treatment.

Mice.

In Vivo Biodistribution with Imaging

Female nude mice were purchased from Charles River Laboratories. Half of the mice (n=6) were injected with 5 million MDA-MB-231 cells in a 100 µL suspension of 50% HBSS and 50% Matrigel (#354234, Corning, Corning NY, USA). Mice were imaged when they had a palpable tumor, and non-tumor bearing mice were imaged as the control. Treatment of hSFRP2 mAb or IgG1 control was administered via tail-vein injections at a concentration of 4 mg/kg. In vivo Study of hSFRP2 mAb Treatment in an Orthotopic Triple Negative Breast Cancer Model Female nude mice were purchased from Envigo at 8 weeks of age. Mice were injected with 5 million MDA-MB-231 cells in a 100 µL suspension of 50% HBSS and 50% basement membrane HC Matrigel phenol red free (#354262, Corning, Corning NY, USA) in the right mammary fat pad. Tumor size was measured every three days with calipers and volumes calculated using the formula (L×W2)/2. Treatment was initiated once tumors approached 50 $mm^3$ in volume at day 19. Mice were randomly distributed into either the IgG1 control treatment group (n=11) or the hSFRP2 mAb treatment group (n=11). Treatments were delivered via tail vein injections at 4 mg/kg iv every 3 days until control tumors reached 2 cm when the experiment was terminated. IgG1 was administered weekly, and the hSFRP2 mAb was administered every three days in accordance with previous MTD and PK studies. Tumor volumes were measured every three days during treatment, and weights were recorded weekly. Treatment concluded at 78 days when control tumors reached a maximum dimension of 2 cm.

Imaging. The Maestro in vivo imaging system was used to evaluate the biodistribution of IgG1 and hSFRP2 mAb in mice through fluorescent labeling of each treatment. Imaging was done prior to injection, immediately after injection, and 24, 48, 72, and 96 hours after injection.

Statistics. Tumor volumes of the IgG1-control group and the hSFRP2 mAb treated group were compared with ANOVA with interactions. Adjustments for multiple comparisons were made using the Sidak technique. A p value<0.05 was considered statistically significant for all analyses. Statistical analyses were completed using the STATA statistical software package (version 15.0).

Egg

Humanized SFRP2 mAb Preferentially Localizes to the Tumor In Vivo

To determine the biodistribution of hSFRP2 mAb treatment in an orthotopic model for triple negative breast cancer, the NIR-tagged hSFRP2 mAb was administered via tail vein injection to tumor-bearing mice and fluorescence was measured by the Maestro in vivo imaging system over 96 hours (FIG. 10). The fluorescence was compared with three non-tumor bearing mice that received the hSFRP2 mAb as a control. At 24 hours, in the tumor-bearing mice, fluorescence was visualized in the liver, bladder, and tumor. Over 72 hours, the fluorescence persisted in the tumor in accordance with its previously determined half-life. Fluorescence dissipated from the liver over this time, and the bladder maintained fluorescence as expected due to urinary excretion. The non-tumor bearing mice did not show fluorescence at the mammary fat pad nor any other specific regions besides the bladder. Tumor-bearing (n=3) and non-tumor-bearing mice (n=3) were administered NIR-tagged IgG1 as a control. The hSFRP2 mAb NIR-tagged showed the distribution of fluorescence in all 3 mice to localize specifically to the tumor, in contrast to the IgG1 NIR-tagged control which did not fluoresce in the tumor.

Humanized SFRP2 mAb Inhibits Tumor Growth In Vivo

To evaluate whether the hSFRP2 mAb inhibits tumor growth in vivo, an orthotopic triple negative breast cancer model of MDA-MB-231 cells in the mammary fat pad of nude mice was used. Treatment commenced when tumor volume reached 50 $mm^3$ at day 19 after tumor cell inoculation. Mice were injected via tail vein with either hSFRP2 mAb (4 mg/kg every 3 days, n=11) or IgG1 control (4 mg/kg weekly, n=11) for 11 weeks. Tumors were measured every three days with calipers, and the volumes calculated (L×W^2)/2. Over the course of treatment, one IgG1-control treated mouse expired early due to ascites. This mouse had no primary tumor on autopsy and was excluded from the study. At the conclusion of the study, one mouse from each treatment group was also excluded due to no tumor present on autopsy. The mean tumor volume at the end of the experiment was 2998 mm$^3$ (n=9, 95% CI) in the IgG1 control group and 1159 mm$^3$ (n=10, 95% CI 800-1519 mm$^3$) in the hSFRP2 group. The hSFRP2mAb treated group had a 61% reduction in tumor volume, which was a significant reduction in tumor volume compared to the IgG1 control group (p<0.001, FIG. 11A). At autopsy, four IgG1 control-treated mice (40%) had distant metastases and one hSFRP2-treated mouse had a distant metastasis (10%) (FIG. 11B). There was no significant weight loss, hair loss, or lethargy in any of the mice over the course of treatment (FIG. 11C).

The invention is not to be limited in scope by the specific aspects described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

```
                           SEQUENCE LISTING

Sequence total quantity: 24
SEQ ID NO: 1            moltype = AA  length = 120
FEATURE                 Location/Qualifiers
REGION                  1..120
                        note = Artificially synthesized Heavy Chain Variable 1
source                  1..120
                        mol_type = protein
                        organism = synthetic construct
SEQUENCE: 1
QVQLVQSGAE LKKPGASVKV SCKASGFTFT RYWWHWVRQA PGKGLEWIGR IDPNSGTTRF  60
IEKFKTRATI TVDKSTSTAY MHLSSLRSED SAVYYCARWG PYYGYAMDYW GQGTSVTVSS 120

SEQ ID NO: 2            moltype = AA  length = 120
FEATURE                 Location/Qualifiers
REGION                  1..120
                        note = Artificially synthesized Heavy Chain Variable 2
source                  1..120
                        mol_type = protein
                        organism = synthetic construct
SEQUENCE: 2
QVQLVQSGAE LKKPGASVKV SCKASGFTFT RYWWHWVRQA PGKGLEWIGR IDPNSGTTRF  60
IEKFKTRATI TVDKSTSTAY MELSSLRSED SAVYYCARWG PYYGYAMDYW GQGTSVTVSS 120

SEQ ID NO: 3            moltype = AA  length = 120
FEATURE                 Location/Qualifiers
REGION                  1..120
                        note = Artificially synthesized Heavy Chain Variable 3
source                  1..120
                        mol_type = protein
                        organism = synthetic construct
SEQUENCE: 3
QVQLVQSGAE VKKPGASVKV SCKASGFTFT RYWWHWVRQA PGKGLEWIGR IDPNSGTTRF  60
IEKFKTRATI TVDKSTSTAY MELSSLRSED TAVYYCARWG PYYGYAMDYW GQGTLVTVSS 120

SEQ ID NO: 4            moltype = AA  length = 120
FEATURE                 Location/Qualifiers
REGION                  1..120
                        note = Artificially synthesized Heavy Chain Variable 4
source                  1..120
                        mol_type = protein
                        organism = synthetic construct
SEQUENCE: 4
QVQLVQSGAE VKKPGASVKV SCKASGFTFT RYWWHWVRQA PGKGLEWIGR IDPNSGTTRF  60
IEKFKTRVTI TVDKSTSTAY MELSSLRSED TAVYYCARWG PYYGYAMDYW GQGTLVTVSS 120

SEQ ID NO: 5            moltype = AA  length = 106
FEATURE                 Location/Qualifiers
REGION                  1..106
                        note = Artificially synthesized Light Variable Chain 1
source                  1..106
                        mol_type = protein
                        organism = synthetic construct
SEQUENCE: 5
QIVLTQSPAI LSLSPGERVT ITCSASSSVT YMHWYQQKLG KAPKLWIYDT SRLAPGSPAR  60
FSGSGSGTDY TLTISSLETE DFASYFCHQW STYPPTFGQG TKLEIK             106

SEQ ID NO: 6            moltype = AA  length = 106
FEATURE                 Location/Qualifiers
REGION                  1..106
                        note = Artificially synthesized Light Variable Chain 2
```

```
                        source             1..106
                                           mol_type = protein
                                           organism = synthetic construct
SEQUENCE: 6
QIVLTQSPAT LSLSPGERVT ITCSASSSVT YMHWYQQKLG KAPKLWIYDT SRLAPGSPAR    60
FSGSGSGTDY TLTISSLESE DFASYFCHQW STYPPTFGQG TKLEIK                  106

SEQ ID NO: 7            moltype = AA    length = 106
FEATURE                 Location/Qualifiers
REGION                  1..106
                        note = Artificially synthesized Light Variable Chain 3
source                  1..106
                        mol_type = protein
                        organism = synthetic construct
SEQUENCE: 7
QIVLTQSPAT LSLSPGERVT ITCSASSSVT YMHWYQQKPG KAPKLWIYDT SRLAPGSPAR    60
FSGSGSGTDY TLTISSLESE DFASYFCHQW STYPPTFGQG TKLEIK                  106

SEQ ID NO: 8            moltype = AA    length = 106
FEATURE                 Location/Qualifiers
REGION                  1..106
                        note = Artificially synthesized Light Variable Chain 4
source                  1..106
                        mol_type = protein
                        organism = synthetic construct
SEQUENCE: 8
QIVLTQSPAT LSLSPGERVT ITCSASSSVT YMHWYQQKPG KAPKLWIYDT SRLAPGSPAR    60
FSGSGSGTDY TLTISSLESE DFATYFCHQW STYPPTFGQG TKLEIK                  106

SEQ ID NO: 9            moltype = AA    length = 106
FEATURE                 Location/Qualifiers
REGION                  1..106
                        note = Artificially synthesized Light Variable Chain 5
source                  1..106
                        mol_type = protein
                        organism = synthetic construct
SEQUENCE: 9
QIVLTQSPAT LSLSPGERVT ITCSASSSVT YMHWYQQKPG KAPKLLIYDT SRLAPGSPAR    60
FSGSGSGTDY TLTISSLESE DFATYFCHQW STYPPTFGQG TKLEIK                  106

SEQ ID NO: 10           moltype = AA    length = 120
FEATURE                 Location/Qualifiers
REGION                  1..120
                        note = Artificially synthesized 80.8.6 Mouse 1 Heavy Chain
source                  1..120
                        mol_type = protein
                        organism = synthetic construct
SEQUENCE: 10
QVQLQQPGAE LVQPGASVML SCKASGFTFT RYWWHWVRQT PGRGLEWIGR IDPNSGTTRF    60
IEKFKTKATL TVDKPSSTAY MHLSSLTSED SAVYYCARWG PYYGYAMDYW GPGTSVTVSS   120

SEQ ID NO: 11           moltype = AA    length = 106
FEATURE                 Location/Qualifiers
REGION                  1..106
                        note = Artificially synthesized 80.8.6 Mouse 1 Light Chain
source                  1..106
                        mol_type = protein
                        organism = synthetic construct
SEQUENCE: 11
QIVLTQSPAI MSASPGQKVT ITCSASSSVT YMHWYQQKLG SSPKLWIYDT SRLAPGSPAR    60
FSGSGSGTSY SLTISSMETE DAASYFCHQW STYPPTFGTG TKLEIQ                  106

SEQ ID NO: 12           moltype = AA    length = 295
FEATURE                 Location/Qualifiers
REGION                  1..295
                        note = Artificially synthesized Secreted Frizzled Related
                         Protein 2
source                  1..295
                        mol_type = protein
                        organism = synthetic construct
SEQUENCE: 12
MLQGPGSLLL LFLASHCCLG SARGLFLFGQ PDFSYKRSNC KPIPVNLQLC HGIEYQNMRL    60
PNLLGHETMK EVLEQAGAWI PLVMKQCHPD TKKFLCSLFA PVCLDDLDET IQPCHSLCVQ   120
VKDRCAPVMS AFGFPWPDML ECDRFPQDND LCIPLASSDH LLPATEEAPK VCEACKNKND   180
DDNDIMETLC KNDFALKIKV KEITYINRDT KIILETKSKT IYKLNGVSER DLKKSVLWLK   240
DSLQCTCEEM NDINAPYLVM GQKQGGELVI TSVKRWQKGQ REFKRISRSI RKLQC        295

SEQ ID NO: 13           moltype = AA    length = 106
FEATURE                 Location/Qualifiers
```

```
REGION                      1..106
                            note = Artificially synthesized Chimeric K Light Chain
source                      1..106
                            mol_type = protein
                            organism = synthetic construct
SEQUENCE: 13
QIVLTQSPAI MSASPGQKVT ITCSASSSVT YMHWYQQKLG SSPKLWIYDT SRLAPGSPAR   60
FSGSGSGTSY SLTISSMETE DAASYFCHQW STYPPTFGTG TKLEIK                 106

SEQ ID NO: 14               moltype = AA  length = 19
FEATURE                     Location/Qualifiers
REGION                      1..19
                            note = Artificially synthesized Peptide B
source                      1..19
                            mol_type = protein
                            organism = synthetic construct
SEQUENCE: 14
NDFALKIKVK EITYINRDT                                               19

SEQ ID NO: 15               moltype = AA  length = 450
FEATURE                     Location/Qualifiers
REGION                      1..450
                            note = Artificially synthesized Heavy Chain
source                      1..450
                            mol_type = protein
                            organism = synthetic construct
SEQUENCE: 15
QVQLVQSGAE LKKPGASVKV SCKASGFTFT RYWWHWVRQA PGKGLEWIGR IDPNSGTTRF   60
IEKFKTRATI TVDKSTSTAY MELSSLRSED SAVYYCARWG PYYGYAMDYW GQGTSVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 16               moltype = AA  length = 213
FEATURE                     Location/Qualifiers
REGION                      1..213
                            note = Artificially synthesized Light Chain
source                      1..213
                            mol_type = protein
                            organism = synthetic construct
SEQUENCE: 16
QIVLTQSPAT LSLSPGERVT ITCSASSSVT YMHWYQQKPG KAPKLLIYDT SRLAPGSPAR   60
FSGSGSGTDY TLTISSLESE DFATYFCHQW STYPPTFGQG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 17               moltype = DNA  length = 1353
FEATURE                     Location/Qualifiers
misc_feature                1..1353
                            note = Artificially synthesized Heavy Chain Nucleotide
                                Sequence
source                      1..1353
                            mol_type = other DNA
                            organism = synthetic construct
SEQUENCE: 17
caggtccaac tggtgcagtc tggggctgag cttaaaaagc ctggggcttc agtgaaggtg   60
tcctgcaagg cttctggctt caccttcacc cgctactggt ggcactgggt gcgccaggcc  120
cctggaaagg gccttgagtg gattggaagg attgatccta atagtggtac cactcgcttc  180
atcgagaagt tcaagacccg cgccacaatc actgtagaca atccaccagc acagcctac  240
atggaactca gcagcctgcg ctctgaggac tctgcggtct attattgtgc aagatgggga  300
ccttattacg gctatgctat ggactactgg ggtcaaggaa ccgcagtcac cgtctcctca  360
gcctccacca agggcccatc ggtcttcccc ctggcaccct ctagcaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggaccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc 1020
aaagccaaag gcagccccg agaaccacag gtgtacaccc tgcccccatc ccgggatgag 1080
ctgaccaaga accaggtcag cctgacctgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctat agcaagctca ccgtggacaa gagcaggtgg 1260
```

```
cagcagggga acgtcttctc atgctccgtg atgcatgagg ctctgcacaa ccactacacg  1320
cagaagagcc tctccctgtc tcccgggaaa tga                                1353

SEQ ID NO: 18          moltype = DNA  length = 642
FEATURE                Location/Qualifiers
misc_feature           1..642
                       note = Artificially synthesized Light Chain Nucleotide
                        Sequence
source                 1..642
                       mol_type = other DNA
                       organism = synthetic construct
SEQUENCE: 18
caaattgttc tcacccagtc tccagcaacc ctgtctttgt ctcctgggga aagagtcacc  60
ataacctgca gtgccagctc aagtgtaacc tacatgcact ggtaccagca gaagccaggc  120
aaagccccca aactcttgat ttatgacaca tccggctgg ctcctggatc tcctgctcgc  180
ttctccggca gtgggtctgg gaccgactac accctcacaa tcagcagcct agagtctgaa  240
gatttcgcca cttatttctg ccatcagtgg agtaccacc cacccacgtt cggtcagggg  300
accaagctgg agatcaaacg aactgtggct gcaccatctg tcttcatctt cccgccatct  360
gatgagcagc ttaagtccgg aactgctagc gttgtgtgcc tgctgaataa cttctatccc  420
agagaggcca agtacagtg gaaggtggat aacgccctcc aatcgggaaa ctcccaggag  480
agtgtcacag agcaggacag caaggacagc acctacagcc tcagcagcac cctgacgctg  540
agcaaagcag actacgagaa acacaaagtc tacgcctgcg aagtcaccca tcagggcctg  600
agctcgcccg tcacaaagag cttcaacagg ggagagtgtt ag                     642

SEQ ID NO: 19          moltype = AA  length = 5
FEATURE                Location/Qualifiers
REGION                 1..5
                       note = Artificially synthesized Ab8 CDR H1
source                 1..5
                       mol_type = protein
                       organism = synthetic construct
SEQUENCE: 19
RYWWH                                                               5

SEQ ID NO: 20          moltype = AA  length = 17
FEATURE                Location/Qualifiers
REGION                 1..17
                       note = Artificially synthesized Ab8 CDR H2
source                 1..17
                       mol_type = protein
                       organism = synthetic construct
SEQUENCE: 20
RIDPNSGTTR FIEKFKT                                                  17

SEQ ID NO: 21          moltype = AA  length = 11
FEATURE                Location/Qualifiers
REGION                 1..11
                       note = Artificially synthesized Ab8 CDR H3
source                 1..11
                       mol_type = protein
                       organism = synthetic construct
SEQUENCE: 21
WGPYYGYAMD Y                                                        11

SEQ ID NO: 22          moltype = AA  length = 10
FEATURE                Location/Qualifiers
REGION                 1..10
                       note = Artificially synthesized Ab8 CDR L1
source                 1..10
                       mol_type = protein
                       organism = synthetic construct
SEQUENCE: 22
SASSSVTYMH                                                          10

SEQ ID NO: 23          moltype = AA  length = 7
FEATURE                Location/Qualifiers
REGION                 1..7
                       note = Artificially synthesized Ab8 CDR L2
source                 1..7
                       mol_type = protein
                       organism = synthetic construct
SEQUENCE: 23
DTSRLAP                                                             7

SEQ ID NO: 24          moltype = AA  length = 9
FEATURE                Location/Qualifiers
REGION                 1..9
                       note = Artificially synthesized Ab8 CDR L3
source                 1..9
```

```
                    mol_type = protein
                    organism = synthetic construct
SEQUENCE: 24
HQWSTYPPT                                                        9
```

What is claimed is:

1. A method of treating cancer in a patient, the method comprising administering to the patient a pharmaceutical composition comprising a therapeutically effective amount of a humanized anti-secreted frizzled-related protein 2 (SFRP2) antibody or antigen binding fragment thereof which binds SFRP2, wherein said humanized antibody or antigen binding fragment thereof comprises a variable heavy (VH) chain polypeptide and a variable light (VL) chain polypeptide comprising the amino acid sequences of SEQ ID NO: 2 and SEQ ID NO: 9, respectively, and a pharmaceutically acceptable excipient.

2. The method of claim 1, wherein the cancer is a breast cancer, an angiosarcoma, an osteosarcoma, a rhabdomyosarcoma, an alveolar soft part sarcoma, a malignant glioma, a multiple myeloma, a renal cell carcinoma, a kidney cancer, a prostate cancer, a lung cancer, a melanoma, a non-small cell lung cancer, a pancreatic cancer, a colorectal cancer, a bladder cancer, a hepatocellular carcinoma, a sarcoma, or a gastrointestinal cancer.

3. The method of claim 1, further comprising administering an antagonist of an inhibitory immune checkpoint molecule, wherein the inhibitory immune checkpoint molecule is PD-1.

4. The method of claim 3, wherein the antagonist of PD-1 is an anti-PD-1 antibody or antigen-binding fragment thereof.

5. The method of claim 4, wherein the anti-PD-1 antibody or antigen-binding fragment thereof is nivolumab, pembrolizumab, MEDI-0680 (AMP-514), camrelizumab (SHR-1210), tislelizumab (BGB-A317), or spartalizumab (NPVPDR001, NVS240118, PDR001).

* * * * *